US008642649B2

(12) United States Patent
Tanoue et al.

(10) Patent No.: US 8,642,649 B2
(45) Date of Patent: *Feb. 4, 2014

(54) ORALLY DISPERSIBLE TABLET

(71) Applicant: Takeda Pharmaceutical Company Limited, Osaka (JP)

(72) Inventors: Yutaka Tanoue, Zurich (CH); Tetsuya Matsuura, Osaka (JP); Yutaka Yamagata, Osaka (JP); Naoki Nagahara, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,788

(22) Filed: Oct. 9, 2012

(65) Prior Publication Data

US 2013/0035385 A1 Feb. 7, 2013

Related U.S. Application Data

(63) Continuation of application No. 13/557,786, filed on Jul. 25, 2012, which is a continuation-in-part of application No. 13/491,887, filed on Jun. 8, 2012, which is a continuation of application No. 13/261,266, filed as application No. PCT/JP2012/051279 on Jan. 16, 2012.

(30) Foreign Application Priority Data

Jan. 17, 2011 (JP) .................................. 2011-007371
Oct. 14, 2011 (JP) .................................. 2011-227333

(51) Int. Cl.
*A01N 43/08* (2006.01)
*A61K 31/34* (2006.01)
*C07D 307/92* (2006.01)
*C07D 307/93* (2006.01)

(52) U.S. Cl.
USPC .......................................... 514/468; 549/458

(58) Field of Classification Search
USPC .......................................... 514/468; 549/458
See application file for complete search history.

(56) References Cited

U.S. PATENT DOCUMENTS

| | | | |
|---|---|---|---|
| 6,034,239 | A | 3/2000 | Ohkawa et al. |
| 6,663,883 | B1 | 12/2003 | Akiyama et al. |
| 2001/0014340 | A1 | 8/2001 | Ohta et al. |
| 2005/0131071 | A1 | 6/2005 | Wuthrich et al. |
| 2007/0134331 | A1 | 6/2007 | Julien et al. |
| 2009/0042861 | A1 | 2/2009 | Hirai et al. |
| 2010/0098756 | A1 | 4/2010 | Matsuoka et al. |
| 2010/0119601 | A1 | 5/2010 | McCarty |
| 2011/0130428 | A1 | 6/2011 | Lindahl et al. |

FOREIGN PATENT DOCUMENTS

| | | |
|---|---|---|
| EP | 1 153 616 A1 | 11/2001 |
| EP | 1 867 641 A1 | 12/2007 |
| JP | 2005-523253 A | 8/2005 |
| JP | 2007-182440 A | 7/2007 |
| WO | WO 97/47287 A1 | 12/1997 |
| WO | WO 99/59544 A2 | 11/1999 |
| WO | WO 00/47233 A1 | 8/2000 |
| WO | WO 01/15735 A1 | 3/2001 |
| WO | WO 01/76565 A1 | 10/2001 |
| WO | WO 2007/137227 A1 | 11/2007 |
| WO | WO 2008/120548 A2 | 10/2008 |
| WO | WO 2008/083204 A2 | 7/2009 |

OTHER PUBLICATIONS

Muller-Oerlinghausen et. al., The Lancet, 2002, The Lancet Publishing Group, vol. 359, pp. 241-247.*
Hilty et. al., Psychiatry (Edgmont), 2006, PubMed, vol. 3, issue 9, pp. 43-55.*
http://www.medterms.com/script/main/art.asp?articlekey=12063.*
http://www.webmd.com/bipolar-disorder/tc/bipolar-disorder-prevention.*
Citrome, L., "Asenapine for schizophrenia and bipolar disorder: a review of the efficacy and safety profile for this newly approved sublingually absorbed second-generation antipsychotic," Int. J. Clin. Pract., Dec. 2009 [epub Oct. 14, 2009], 63(12):1762-1784.
Vogt et al., "Pharmacokinetics and haemodynamic effects of ISDN following different dosage forms and routes of administration," European Journal of Clinical Pharmacology, 1994, 46(4):319-324.
ClinicalTrials.gov, NCT00552760, "Ramelteon for the Treatment of Insomnia and Mood Stability in Patients with Euthymic Bipolar Disorder (Ram-TIME)," First received Oct. 31, 2007, last updated Jun. 1, 2010, 14 pages.
Hilty et al., "A Review of Bipolar Disorder in Adults," Psychiatry, Sep. 2006, 3(9):43-55.
http://www.medterms.com/script/main/art.asp?articlekey=12063 (prior U.S. Appl. No. 13/491,887), Aug. 6, 2012.
http://www.webmd.com/bipolar-disorder/tc/bipolar-disorder-prevention (prior U.S. Appl. No. 13/491,887), Aug. 6, 2012.
Kurosaki et al "Drug Absorption From Oral Mucosa—mechanism and enhancers," Igaku no ayumi, 1988, 145(7):468-470, with English translation.

* cited by examiner

*Primary Examiner* — Sarah Pihonak
(74) *Attorney, Agent, or Firm* — Foley & Lardner LLP

(57) ABSTRACT

The present invention provides a preparation with improved disintegration property, a preparation showing improved bioavailability of a medicament, production methods thereof and the like. A rapidly disintegrating preparation comprising granules comprising a medicament coated with a coating layer containing sugar or sugar alcohol; and a disintegrant. A production method of a rapidly disintegrating preparation including a step of producing granules comprising a medicament, a step of forming a coating layer containing sugar or sugar alcohol on the obtained granules and a step of mixing the coated granules with a disintegrant and molding the mixture.

24 Claims, 2 Drawing Sheets

ORALLY DISPERSIBLE TABLET

TECHNICAL FIELD OF THE INVENTION

The present invention relates to a preparation with improved disintegration property, a preparation with improved bioavailability of medicament, production methods thereof and the like.

BACKGROUND OF THE INVENTION

Patent document 1 discloses a tablet containing sugar alcohol or saccharide having an average particle size of 30 μm or below, an active ingredient and a disintegrant, and a production method of a tablet comprising compression molding a mixture containing sugar alcohol or sugar having an average particle size of 30 μm or below, an active ingredient and a disintegrant.

Patent document 2 discloses an orally dispersible solid pharmaceutical composition of agomelatine, which contains agomelatine and granules of simultaneously-dried lactose and starch.

Patent document 3 discloses an orally dispersible, coated solid pharmaceutical composition of agomelatine, which contains a central core or a central layer comprising agomelatine and excipients allowing an orally dispersible formulation to be obtained, and an orally dispersible coating.

DOCUMENT LIST

Patent Documents patent document 1: WO1997/047287
patent document 2: JP-A-2005-523253
patent document 3: JP-A-2007-182440

SUMMARY OF THE INVENTION

Exemplary Problems to be Solved by the Invention

An object of the present invention is to provide a preparation capable of promoting medicament absorption from the oral mucosa by rapid disintegration after sublingual or buccal administration. Such preparations have benefits over oral (but not sublingual or buccal) administration of the same medicament, including improving bioavailability, providing a lower ratio of metabolite to medicament, increasing Cmax, decreasing Tmax, increasing AUC(0-tlqc) and increasing the coefficient of variance for Cmax and AUC(0-tlqc). Such preparations also are useful for treating bipolar disorder generally, as well as the remission and depression phases of the disorder.

Another object of the present invention is to provide a novel formulation technique capable of improving disintegration property. In addition, another object of the present invention is to provide a preparation useful as an orally rapidly disintegrating preparation. Such objects are not limiting to the invention and are merely exemplary.

Means of Solving the Problems

Formulation: A Rapidly Disintegrating Preparation

The present inventors have conducted intensive studies in an attempt to solve the aforementioned problems and found that the disintegration property of a medicament can be improved and the bioavailability thereof can also be improved by containing a component that prevents disintegration (masking agent, binder and the like) as a granulation component in granules, and formulating the preparation after coating a surface of the granule with sugar or sugar alcohol, which resulted in the completion of the present invention.

Accordingly, the present invention provides the following.
[1] A rapidly disintegrating preparation comprising granules comprising a medicament coated with a coating layer containing sugar or sugar alcohol; and a disintegrant (hereinafter sometimes to be abbreviated as preparation [1], the same for the following [2] to [18], and [37] to [69]).
[2] The rapidly disintegrating preparation of the above-mentioned [1], wherein the granules comprising a medicament further contains a binder.
[3] The rapidly disintegrating preparation of the above-mentioned [1], wherein the granules comprising a medicament further contains a masking agent.
[4] The rapidly disintegrating preparation of the above-mentioned [1], wherein the granules comprising a medicament further contains a solubilizer.
[4-1] The rapidly disintegrating preparation of any of the above-mentioned [1]-[4], wherein the disintegration time is not more than 30 sec.
[4-2] The rapidly disintegrating preparation of any of the above-mentioned [1]-[4], wherein the disintegration time is not more than 30 sec and the absolute hardness is not less than 1.0 N/mm$^2$.

The "rapidly disintegrating preparation" of the present invention is also superior as a preparation for allowing absorption of a medicament from the oral mucosa. Specifically, it is as described below.
[5] The preparation of any of the above-mentioned [1]-[4], which is for oral-mucosal absorption. The terms "oral-mucosal" and "oral-mucosa" in the context of drug delivery, as used herein connotes administration of a medicament directly to the mucosal lining of the oral cavity, e.g., by a sublingual or buccal route, such that the medicament enters the systemic circulation and substantially bypasses hepatic first pass metabolism. The term "oral" in the context of drug delivery, as used herein connotes administration of a medicament to the oral cavity but not directly to the mucosa lining the oral cavity. The medicament that is delivered by the oral route (in contrast to the oral-mucosal route) enters the systemic circulation after absorption in the gastrointestinal tract.
[6] The preparation of the above-mentioned [5], wherein the medicament is (S)—N-[2-(1,6,7,8-tetrahydro-2H-indeno[5,4-b]furan-8-yl)ethyl]propionamide (general name ramelteon; hereinafter sometimes to be abbreviated as compound A).
[7] The preparation of the above-mentioned [5] or [6], which is a tablet.
[8] A method of producing a rapidly disintegrating preparation, comprising a step of producing granules comprising a medicament.
a step of forming a coating layer containing sugar or sugar alcohol on the obtained granules, and
a step of mixing the coated granules with a disintegrant and molding the mixture.
Formulation: A Preparation for Oral-Mucosal Absorption of Compound A In addition to the above-mentioned preparation [6], the present inventors have conducted intensive studies of a preparation superior in the absorption of compound A from the oral mucosa, and showing improved bioavailability thereof:
[9] A preparation for oral-mucosal absorption comprising (S)—N-[2-(1,6,7,8-tetrahydro-2H-indeno[5,4-b]furan-8-yl)ethyl]propionamide as a medicament; which shows a higher ratio of the medicament in an unchanged form and a metabolite of the medicament (i.e., medicament in unchanged form/metabolite of the medicament) after transfer into blood than that by oral administration.

(here and hereinafter, "a metabolite of the medicament" means, in particular, (2S)-2-hydroxy-N-{2-[(BS)-1,6,7,8-tetrahydro-2H-indeno[5,4-b]furan-8-yl]ethyl}propanamide, which is known as M-II.)

[10] A preparation for oral-mucosal absorption comprising (S)—N-[2-(1,6,7,8-tetrahydro-2H-indeno[5,4-b]furan-8-yl)ethyl]propionamide as a medicament; which shows a higher ratio of the medicament in an unchanged form and a metabolite of the medicament after transfer into blood than that by oral administration, and a disintegration time of not more than 30 sec.

[11] A preparation for oral-mucosal absorption comprising (S)—N-[2-(1,6,7,8-tetrahydro-2H-indeno[5,4-b]furan-8-yl)ethyl]propionamide as a medicament; which shows a higher ratio of the medicament in an unchanged form and a metabolite of the medicament after transfer into blood than that by oral administration, a disintegration time of not more than 30 sec, and absolute hardness of not less than $1.0 \text{ N/mm}^2$.

[12] A preparation for oral-mucosal absorption comprising (S)—N-[2-(1,6,7,8-tetrahydro-2H-indeno[5,4-b]furan-8-yl)ethyl]propionamide and a masking agent; which shows not less than about 10-fold improved bioavailability of (S)—N-[2-(1,6,7,8-tetrahydro-2H-indeno[5,4-b]furan-8-yl)ethyl]propionamide, as compared to that by oral administration.

[13] A preparation for oral-mucosal absorption comprising (S)—N-[2-(1,6,7,8-tetrahydro-2H-indeno[5,4-b]furan-8-yl)ethyl]propionamide and a masking agent; which shows not less than about 10-fold improved bioavailability of (S)—N-[2-(1,6,7,8-tetrahydro-2H-indeno[5,4-b]furan-8-yl)ethyl]propionamide, as compared to that by oral administration, and a disintegration time of not more than 30 sec.

[14] A preparation for oral-mucosal absorption comprising (S)—N-[2-(1,6,7,8-tetrahydro-2H-indeno[5,4-b]furan-8-yl)ethyl]propionamide and a masking agent; which shows not less than about 10-fold improved bioavailability of (S)—N-[2-(1,6,7,8-tetrahydro-2H-indeno[5,4-b]furan-8-yl)ethyl]propionamide, as compared to that by oral administration, a disintegration time of not more than 30 sec, and absolute hardness of not less than $1.0 \text{ N/mm}^2$.

[15] A preparation for oral-mucosal absorption comprising (S)—N-[2-(1,6,7,8-tetrahydro-2H-indeno[5,4-b]furan-8-yl)ethyl]propionamide, sugar or sugar alcohol, and a disintegrant; which shows not less than about 10-fold improved bioavailability of (S)—N-[2-(1,6,7,8-tetrahydro-2H-indeno[5,4-b]furan-8-yl)ethyl]propionamide, as compared to that by oral administration, and a disintegration time of not more than 30 sec.

[16] A preparation for oral-mucosal absorption comprising (S)—N-[2-(1,6,7,8-tetrahydro-2H-indeno[5,4-b]furan-8-yl)ethyl]propionamide, sugar or sugar alcohol, and a disintegrant; which shows not less than about 10-fold improved bioavailability of (S)—N-[2-(1,6,7,8-tetrahydro-2H-indeno[5,4-b]furan-8-yl)ethyl]propionamide, as compared to that by oral administration, a disintegration time of not more than 30 sec, and absolute hardness of not less than $1.0 \text{ N/mm}^2$.

[17] The preparation of any of the above-mentioned [9]-[16], which is a tablet.

[18] The preparation of the above-mentioned [9] or [12], which is in the form of a film, troche, solution, suspension, freeze-dried preparation, chewing gum or spray.

Method of Use of Compound A: Prophylaxis and/or Treatment of a Bipolar Disorder (1)

The present invention also relates to a method of use of compound A for prophylaxis and/or treatment of a bipolar disorder by administering it to a human in need thereof oral-mucosally.

[19] A method for the prophylaxis and/or treatment of a bipolar disorder comprising administering (S)—N-[2-(1,6,7,8-tetrahydro-2H-indeno[5,4-b]furan-8-yl)ethyl]propionamide oral-mucosally to a human.

(hereinafter sometimes to be abbreviated as method [19], the same for the following [20] to [23], [28], [34], and [70] to [110]).

[20] The method of the above-mentioned [19], wherein the oral-mucosal administration is sublingual administration or buccal administration (more preferably sublingual administration).

[21] The method of the above-mentioned [19], wherein (S)—N-[2-(1,6,7,8-tetrahydro-2H-indeno[5,4-b]furan-8-yl)ethyl]propionamide is administered in 0.05-1.0 mg per day.

[22] The method of the above-mentioned [19], wherein the bipolar disorder is bipolar disorder I.

[23] The method of the above-mentioned [19], wherein the prophylaxis and/or treatment of a bipolar disorder is a treatment of a depression symptom associated with the bipolar disorder or maintenance of a remission phase of the bipolar disorder.

[24] A drug for the prophylaxis and/or treatment of a bipolar disorder, which comprises, as an active ingredient, (S)—N-[2-(1,6,7,8-tetrahydro-2H-indeno[5,4-b]furan-8-yl)ethyl]propionamide to be oral-mucosally administered to a human.

(hereinafter sometimes to be abbreviated as drug [24], the same for the following [25] to [27], and [35]).

[25] The drug of the above-mentioned [24], wherein the oral-mucosal administration is sublingual administration or buccal administration (more preferably sublingual administration).

[26] The drug of the above-mentioned [24], wherein (S)—N-[2-(1,6,7,8-tetrahydro-2H-indeno[5,4-b]furan-8-yl)ethyl]propionamide is administered in 0.05-1.0 mg per day.

[27] The drug of the above-mentioned [24], wherein the bipolar disorder is bipolar disorder I.

[28] The method of the above-mentioned [24], wherein the prophylaxis and/or treatment of a bipolar disorder is a treatment of a depression symptom associated with the bipolar disorder or maintenance of a remission phase of the bipolar disorder.

[29] (S)—N-[2-(1,6,7,8-tetrahydro-2H-indeno[5,4-b]furan-8-yl)ethyl]propionamide for the prophylaxis and/or treatment of a bipolar disorder by oral-mucosal administration to a human. (hereinafter sometimes to be abbreviated as compound [29], the same for the following [30] to [33], and [36]).

[30] The (S)—N-[2-(1,6,7,8-tetrahydro-2H-indeno[5,4-b]furan-8-yl)ethyl]propionamide of the above-mentioned [29], wherein the oral-mucosal administration is sublingual administration or buccal administration (more preferably sublingual administration).

[31] The (S)—N-[2-(1,6,7,8-tetrahydro-2H-indeno[5,4-b]furan-8-yl)ethyl]propionamide of the above-mentioned [29], which is administered in 0.05-1.0 mg per day.

[32] The (S)—N-[2-(1,6,7,8-tetrahydro-2H-indeno[5,4-b]furan-8-yl)ethyl]propionamide of the above-mentioned [29], wherein the bipolar disorder is bipolar disorder I.

[33] The (S)—N-[2-(1,6,7,8-tetrahydro-2H-indeno[5,4-b]furan-8-yl)ethyl]propionamide of the above-mentioned [29], wherein the prophylaxis and/or treatment of the bipolar disorder is a treatment of a depression symptom associated with the bipolar disorder or maintenance of a remission phase of the bipolar disorder.

[34] The method of the above-mentioned [19]-[23], wherein (S)—N-[2-(1,6,7,8-tetrahydro-2H-indeno[5,4-b]furan-8-yl)ethyl]propionamide is administered as the preparation of the above-mentioned [5]-[7], or [9]-[18].

[35] The drug of the above-mentioned [24]-[28], wherein (S)—N-[2-(1,6,7,8-tetrahydro-2H-indeno[5,4-b]furan-8-yl)ethyl]propionamide is administered as the preparation of the above-mentioned [5]-[7], or [9]-[18].

[36] The (S)—N-[2-(1,6,7,8-tetrahydro-2H-indeno[5,4-b]furan-8-yl)ethyl]propionamide of the above-mentioned [29]-[33], which is administered as the preparation of the above-mentioned [5]-[7], or [9]-[18].

Formulation: A Preparation for Oral-Mucosal Absorption of compound A (2)

Another aspect of the present invention relates to the following "formulations with limitation by dose and/or PK profile".

[37] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.1 mg a day, and (2) the preparation provides to a human subject in a fasting state Cmax for compound A falling within the range of about 0.43 to about 3.13 ng/ml and AUC (0-tlqc) for compound A falling within the range of about 0.48 to about 2.26 ng·hr/ml.

[37-1] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.1 mg a day, and (2) the preparation provides to a human subject in a fasting state Cmax for compound A falling within the range of about 0.43 to about 3.13 ng/ml and AUC (0-tlqc) for compound A falling within the range of about 0.48 to about 2.26 ng·hr/ml, and (3) the average Tmax value of plasma level of compound A after administration to a human is not more than about 0.4 hrs, preferably, not more than about 0.3 hrs, and more preferably, not more than about 0.25 hrs.

[38] The preparation of the afore-mentioned [37], wherein (1) the dose of compound A is 0.1 mg a day, and (2) the preparation provides to a human subject in a fasting state Cmax for compound A falling within the range of about 0.66 to about 2.05 ng/ml and AUC (0-tlqc) for compound A falling within the range of about 0.67 to about 1.62 ng·hr/ml.

[38-1] The preparation of the afore-mentioned [37-1], wherein (1) the dose of compound A is 0.1 mg a day, (2) the preparation provides to a human subject in a fasting state Cmax for compound A falling within the range of about 0.66 to about 2.05 ng/ml and AUC (0-tlqc) for compound A falling within the range of about 0.67 to about 1.62 ng·hr/ml, and (3) the average Tmax value of plasma level of compound A after administration to a human is not more than about 0.4 hrs, preferably, not more than about 0.3 hrs, and more preferably, not more than about 0.25 hrs.

[39] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.4 mg a day, and (2) the preparation provides to a human subject in a fasting state Cmax for compound A falling within the range of about 2.04 to about 6.89 ng/ml and AUC (0-tlqc) for compound A falling within the range of about 1.52 to about 6.68 ng·hr/ml.

[39-1] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.4 mg a day, (2) the preparation provides to a human subject in a fasting state Cmax for compound A falling within the range of about 2.04 to about 6.89 ng/ml and AUC (0-tlqc) for compound A falling within the range of about 1.52 to about 6.68 ng·hr/ml, and (3) the average Tmax value of plasma level of compound A after administration to a human is not more than about 0.4 hrs, preferably, not more than about 0.3 hrs, and more preferably, not more than about 0.25 hrs.

[40] The preparation of the afore-mentioned [39], wherein (1) the dose of compound A is 0.4 mg a day, and (2) the preparation provides to a human subject in a fasting state Cmax for compound A falling within the range of about 2.54 to about 5.54 ng/ml and AUC (0-tlqc) for compound A falling within the range of about 1.98 to about 5.12 ng·hr/ml.

[40-1] The preparation of the afore-mentioned [39-1], wherein (1) the dose of compound A is 0.4 mg a day, (2) the preparation provides to a human subject in a fasting state Cmax for compound A falling within the range of about 2.54 to about 5.54 ng/ml and AUC (0-tlqc) for compound A falling within the range of about 1.98 to about 5.12 ng·hr/ml, and (3) the average Tmax value of plasma level of (S)—N-[2-(1,6,7,8-tetrahydro-2H-indeno[5,4-b]furan-8-yl)ethyl]propionamide after administration to a human is not more than about 0.4 hrs, preferably, not more than about 0.3 hrs, and more preferably, not more than about 0.25 hrs.

[41] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.8 mg a day, and (2) the preparation provides to a human subject in a fasting state Cmax for compound A falling within the range of about 3.63 to about 14.06 ng/ml and AUC (0-tlgc) for compound A falling within the range of about 2.48 to about 14.43 ng·hr/ml.

[41-1] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.8 mg a day, (2) the preparation provides to a human subject in a fasting state Cmax for compound A falling within the range of about 3.63 to about 14.06 ng/ml and AUC (0-tlgc) for compound A falling within the range of about 2.48 to about 14.43 ng·hr/ml, and (3) the average Tmax value of plasma level of (S)—N-[2-(1,6,7,8-tetrahydro-2H-indeno[5,4-b]furan-8-yl)ethyl]propionamide after administration to a human is not more than about 0.4 hrs, preferably, not more than about 0.3 hrs, and more preferably, not more than about 0.25 hrs.

[42] The preparation of the afore-mentioned [41], wherein (1) the dose of compound A is 0.8 mg a day, and (2) the preparation provides to a human subject in a fasting state Cmax for compound A falling within the range of about 4.85 to about 10.54 ng/ml and AUC (0-tlgc) for compound A falling within the range of about 3.60 to about 9.91 ng·hr/ml.

[42-1] The preparation of the afore-mentioned [41-1], wherein (1) the dose of compound A is 0.8 mg a day, (2) the preparation provides to a human subject in a fasting state Cmax for compound A falling within the range of about 4.85 to about 10.54 ng/ml and AUC (0-tlgc) for compound A falling within the range of about 3.60 to about 9.91 ng·hr/ml, and (3) the average Tmax value of plasma level of (S)—N-[2-(1,6,7,8-tetrahydro-2H-indeno[5,4-b]furan-8-yl)ethyl]propionamide after administration to a human is not more than about 0.4 hrs, preferably, not more than about 0.3 hrs, and more preferably, not more than about 0.25 hrs.

[43] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.05-1.0 mg a day; and (2) the AUC ratio of the metabolite of compound A (M-II) to compound A in an unchanged form after administration to a human is not more than about 20.

[44] A preparation for oral-mucosal absorption comprising (S)—N-[2-(1,6,7,8-tetrahydro-2H-indeno[5,4-b]furan-8-yl)ethyl]propionamide (compound A); wherein (1) the dose of compound A is 0.1-0.8 mg a day; and (2) the AUC ratio of the metabolite of compound A (M-II) to compound A in an unchanged form after administration to a human is not more than about 20.

[45] The preparation for oral-mucosal absorption of the afore-mentioned [43], wherein the AUC ratio is not more than about 10.

[46] The preparation for oral-mucosal absorption of the afore-mentioned [44], wherein the AUC ratio is not more than about 10.

[47] A preparation for oral-mucosal absorption comprising (S)—N-[2-(1,6,7,8-tetrahydro-2H-indeno[5,4-b]furan-8-yl)ethyl]propionamide; wherein the AUC ratio of (S)—N-[2-(1,6,7,8-tetrahydro-2H-indeno[5,4-b]furan-8-yl)ethyl]propionamide in an unchanged form to a metabolite of (S)—N-[2-(1,6,7,8-tetrahydro-2H-indeno[5,4-b]furan-8-yl)ethyl]propionamide (M-II) after administration to a human is not less than about 5-fold than that by oral administration.

[48] The preparation for oral-mucosal absorption of the afore-mentioned [47], wherein the AUC ratio is not less than about 10-fold than that by oral administration.

[49] The preparation for oral-mucosal absorption of any of the afore-mentioned [47] or [48], wherein the AUC ratio is not more than about 30-fold, preferably, not more than about 20-fold.

[50] A preparation for oral-mucosal absorption comprising (S)—N-[2-(1,6,7,8-tetrahydro-2H-indeno[5,4-b]furan-8-yl)ethyl]propionamide; wherein the AUC ratio of the metabolite of (S)—N-[2-(1,6,7,8-tetrahydro-2H-indeno[5,4-b]furan-8-yl)ethyl]propionamide (M-II) to (S)—N-[2-(1,6,7,8-tetrahydro-2H-indeno[5,4-b]furan-8-yl)ethyl]propionamide in an unchanged form after administration to a human is not more than about 20.

[51] The preparation for oral-mucosal absorption of afore-mentioned [50], wherein the AUC ratio is not more than about 10, more preferably, not more than about 5.

[52] A preparation for oral-mucosal absorption comprising (S)—N-[2-(1,6,7,8-tetrahydro-2H-indeno[5,4-b]furan-8-yl)ethyl]propionamide; wherein the bioavailability of (S)—N-[2-(1,6,7,8-tetrahydro-2H-indeno[5,4-b]furan-8-yl)ethyl]propionamide is improved not less than about 10-fold than that by oral administration, more specifically, is improved within the range from not less than about 10-fold to not more than about 30-fold than that by oral administration.

[53] A preparation for oral-mucosal absorption comprising (S)—N-[2-(1,6,7,8-tetrahydro-2H-indeno[5,4-b]furan-8-yl)ethyl]propionamide, wherein the average Tmax value of plasma level of (S)—N-[2-(1,6,7,8-tetrahydro-2H-indeno[5,4-b]furan-8-yl)ethyl]propionamide after administration to a human is not more than about 0.4 hrs, preferably, not more than about 0.3 hrs, and more preferably, not more than about 0.25 hrs.

[54] The preparation for oral-mucosal absorption of any of the afore-mentioned [47] to [52], wherein the average Tmax value of plasma level of (S)—N-[2-(1,6,7,8-tetrahydro-2H-indeno[5,4-b]furan-8-yl)ethyl]propionamide after administration to a human is not more than about 0.4 hrs, preferably, not more than about 0.3 hrs, more preferably, not more than about 0.25 hrs.

[55] A preparation for oral-mucosal absorption comprising (S)—N-[2-(1,6,7,8-tetrahydro-2H-indeno[5,4-b]furan-8-yl)ethyl]propionamide, wherein the coefficient of variation (CV) of pharmacokinetic parameters including Cmax and AUC of (S)—N-[2-(1,6,7,8-tetrahydro-2H-indeno[5,4-b]furan-8-yl)ethyl]propionamide after administration to a human is not more than about 45%, preferably, not more than about 35%, and more preferably, not more than about 30%.

[56] The preparation for oral-mucosal absorption of any of the afore-mentioned [47] to [54], wherein the coefficient of variation (CV) of pharmacokinetic parameters including Cmax and AUC of (S)—N-[2-(1,6,7,8-tetrahydro-2H-indeno[5,4-b]furan-8-yl)ethyl]propionamide after administration to a human is not more than about 45%, preferably, not more than about 35%, and more preferably, not more than about 30%.

[57] A preparation for oral-mucosal absorption comprising (S)—N-[2-(1,6,7,8-tetrahydro-2H-indeno[5,4-b]furan-8-yl)ethyl]propionamide; wherein the dose of (S)—N-[2-(1,6,7,8-tetrahydro-2H-indeno[5,4-b]furan-8-yl)ethyl]propionamide is 0.05-1.0 mg a day.

[58] The preparation for oral-mucosal absorption of the afore-mentioned [57], wherein the dose of (S)—N-[2-(1,6,7,8-tetrahydro-2H-indeno[5,4-b]furan-8-yl)ethyl]propionamide is 0.1-0.8 mg a day.

[59] The preparation for oral-mucosal absorption of any of the afore-mentioned [57] or [58], wherein the AUC ratio of (S)—N-[2-(1,6,7,8-tetrahydro-2H-indeno[5,4-b]furan-8-yl)ethyl]propionamide in an unchanged form to a metabolite of (S)—N-[2-(1,6,7,8-tetrahydro-2H-indeno[5,4-b]furan-8-yl)ethyl]propionamide (M-II) after administration to a human is not less than about 5-fold than that by oral administration.

[60] The preparation for oral-mucosal absorption of the afore-mentioned [59], wherein the AUC ratio is not less than about 10-fold than that by oral administration.

[61] The preparation for oral-mucosal absorption of the afore-mentioned [60], wherein the AUC ratio is not less than about 10-fold than that by oral administration.

[62] The preparation for oral-mucosal absorption of any of the afore-mentioned [59] to [61], wherein the AUC ratio is not more than about 30-fold, preferably, not more than about 20-fold.

[63] The preparation for oral-mucosal absorption of afore-mentioned [57] or [58], wherein the AUC ratio of the metabolite of (S)—N-[2-(1,6,7,8-tetrahydro-2H-indeno[5,4-b]furan-8-yl)ethyl]propionamide (M-II) to (S)—N-[2-(1,6,7,8-tetrahydro-2H-indeno[5,4-b]furan-8-yl)ethyl]propionamide in an unchanged form after administration to a human is not more than about 20.

[64] The preparation for oral-mucosal absorption of the afore-mentioned [63], wherein the AUC ratio is not more than about 10.

[65] The preparation for oral-mucosal absorption of any of the afore-mentioned [63] or [64], wherein the AUC ratio is not less than about 5.

[66] The preparation for oral-mucosal absorption of afore-mentioned [57] or [58], wherein the bioavailability of (S)—N-[2-(1,6,7,8-tetrahydro-2H-indeno[5,4-b]furan-B-yl)ethyl]propionamide is improved not less than about 10-fold than that by oral administration, more specifically, is improved within the range from not less than about 10-fold to not more than about 30-fold than that by oral administration.

[67] The preparation for oral-mucosal absorption of any of the afore-mentioned [57] to [66], wherein the average Tmax value of plasma level of (S)—N-[2-(1,6,7,8-tetrahydro-2H-indeno[5,4-b]furan-8-yl)ethyl]propionamide after administration to a human is not more than about 0.4 hrs, preferably, not more than about 0.3 hrs, and more preferably, not more than about 0.25 hrs.

[68] The preparation for oral-mucosal absorption of any of the afore-mentioned [57] to [67], wherein the coefficient of variation (CV) of pharmacokinetic parameters including Cmax and AUC of (S)—N-[2-(1,6,7,8-tetrahydro-2H-indeno[5,4-b]furan-8-yl)ethyl]propionamide after administration to a human is not more than about 45%, preferably, not more than about 35%, and more preferably, not more than about 30%.

[69] The preparation for oral-mucosal absorption of any of the afore-mentioned [57] to [68], wherein the preparation further contains a disintegrant.

Method of Use of Compound A: Prophylaxis and/or Treatment of a Bipolar Disorder (2)

Another aspect of the present invention relates to the following "method of use of compound A with limitation by dose and/or PK profile".

[70] A method for the prophylaxis and/or treatment of a bipolar disorder comprising administering daily 0.05 to 1.0 mg of (S)—N-[2-(1,6,7,8-tetrahydro-2H-indeno[5,4-b]furan-8-yl)ethyl]propionamide to the oral mucosa of a human in need thereof.

[71] The method of the afore-mentioned [70], wherein 0.1 to 0.8 mg of (S)—N-[2-(1,6,7,8-tetrahydro-2H-indeno[5,4-b]furan-8-yl)ethyl]propionamide is administered daily.

[72] The method of any of the afore-mentioned [70] or [71], wherein (S)—N-[2-(1,6,7,8-tetrahydro-2H-indeno[5,4-b]furan-8-yl)ethyl]propionamide is administered by a sublingual route of administration or a buccal route of administration.

[73] A method for the prophylaxis and/or treatment of a bipolar disorder comprising administering daily 0.1 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 0.43 to about 3.13 ng/ml and AUC (0-tlqc) for compound A falls within the range of about 0.48 to about 2.26 ng·hr/ml.

[73-1] A method for the prophylaxis and/or treatment of a bipolar disorder comprising administering daily 0.1 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 0.43 to about 3.13 ng/ml and AUC (0-tlqc) for compound A falls within the range of about 0.48 to about 2.26 ng·hr/ml; and the average Tmax value of plasma level of compound A after administration to a human is not more than about 0.4 hrs, preferably, not more than about 0.3 hrs, and more preferably, not more than about 0.25 hrs.

[74] The method of any of the afore-mentioned [73] or [73-1], wherein the oral-mucosal administration is sublingual administration or buccal administration.

[75] The method of any of the afore-mentioned [73] or [73-1], wherein the bipolar disorder is bipolar disorder I.

[76] The method of any of the afore-mentioned [73] or [73-1], wherein the prophylaxis and/or treatment of a bipolar disorder is a treatment of a depression symptom associated with the bipolar disorder or maintenance of a remission phase of the bipolar disorder.

[77] The method of any of the afore-mentioned [73] or [73-1], wherein in the fasting state, Cmax for compound A falls within the range of about 0.66 to about 2.05 ng/ml and AUC (0-tlqc) for compound A falls within the range of about 0.67 to about 1.62 ng·hr/ml.

[78] The method of the afore-mentioned [77], wherein the oral-mucosal administration is sublingual administration or buccal administration.

[79] The method of the afore-mentioned [77], wherein the bipolar disorder is bipolar disorder I.

[80] The method of the afore-mentioned [77], wherein the prophylaxis and/or treatment of a bipolar disorder is a treatment of a depression symptom associated with the bipolar disorder or maintenance of a remission phase of the bipolar disorder.

[81] A method for the prophylaxis and/or treatment of a bipolar disorder comprising administering daily 0.4 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 2.04 to about 6.89 ng/ml and AUC (0-tlqc) for compound A falls within the range of about 1.52 to about 6.68 ng·hr/ml.

[81-1] A method for the prophylaxis and/or treatment of a bipolar disorder comprising administering daily 0.4 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 2.04 to about 6.89 ng/ml and AUC (0-tlqc) for compound A falls within the range of about 1.52 to about 6.68 ng·hr/ml; and the average Tmax value of plasma level of compound A after administration to a human is not more than about 0.4 hrs, preferably, not more than about 0.3 hrs, and more preferably, not more than about 0.25 hrs.

[82] The method of any of the afore-mentioned [81] or {81-1}, wherein the oral-mucosal administration is sublingual administration or buccal administration.

[83] The method of the afore-mentioned [82] wherein the bipolar disorder is bipolar disorder I.

[84] The method of the afore-mentioned [82], wherein the prophylaxis and/or treatment of a bipolar disorder is a treatment of a depression symptom associated with the bipolar disorder or maintenance of a remission phase of the bipolar disorder.

[85] The method of any of the afore-mentioned [81] or [81-1], wherein in the fasting state, Cmax for compound A falls within the range of about 2.54 to about 5.54 ng/ml and AUC (0-tlqc) for compound A falls within the range of about 1.98 to about 5.12 ng·hr/ml.

[86] The method of the afore-mentioned [85], wherein the oral-mucosal administration is sublingual administration or buccal administration.

[87] The method of the afore-mentioned [85], wherein the bipolar disorder is bipolar disorder I.

[88] The method of the afore-mentioned [85], wherein the prophylaxis and/or treatment of a bipolar disorder is a treatment of a depression symptom associated with the bipolar disorder or maintenance of a remission phase of the bipolar disorder.

[89] A method for the prophylaxis and/or treatment of a bipolar disorder comprising administering daily 0.8 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 3.63 to about 14.06 ng/ml and AUC (0-tlqc) for compound A falls within the range of about 2.48 to about 14.43 ng·hr/ml.

[89-1] A method for the prophylaxis and/or treatment of a bipolar disorder comprising administering daily 0.8 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 3.63 to about 14.06 ng/ml and AUC (0-tlqc) for compound A falls within the range of about 2.48 to about 14.43 ng·hr/ml; and the average Tmax value of plasma level of compound A after administration to a human is not more than about 0.4 hrs, preferably, not more than about 0.3 hrs, and more preferably, not more than about 0.25 hrs.

[90] The method of any of the afore-mentioned [89] or [89-1], wherein the oral-mucosal administration is sublingual administration or buccal administration.

[91] The method of the afore-mentioned [90], wherein the bipolar disorder is bipolar disorder I.

[92] The method of the afore-mentioned [90], wherein the prophylaxis and/or treatment of a bipolar disorder is a treatment of a depression symptom associated with the bipolar disorder or maintenance of a remission phase of the bipolar disorder.

[93] The method of any of the afore-mentioned [89] or [89-1], wherein in the fasting state, Cmax for compound A falls within the range of about 4.85 to about 10.54 ng/ml and AUC (0-tlqc) for compound A falls within the range of 3.60 to about 9.91 ng·hr/ml.

[94] The method of the afore-mentioned [93], wherein the oral-mucosal administration is sublingual administration or buccal administration.

[95] The method of the afore-mentioned [93], wherein the bipolar disorder is bipolar disorder I.

[96] The method of the afore-mentioned [93], wherein the prophylaxis and/or treatment of a bipolar disorder is a treatment of a depression symptom associated with the bipolar disorder or maintenance of a remission phase of the bipolar disorder.

[97] A method for the prophylaxis and/or treatment of a bipolar disorder comprising administering daily 0.05 to 1.0 mg of (S)—N-[2-(1,6,7,8-tetrahydro-2H-indeno[5,4-b]furan-8-yl)ethyl]propionamide (compound A) to the oral mucosa of a human in need thereof, wherein the AUC ratio of a metabolite of compound A (M-II) to compound A in an unchanged form after administration is not more than 20.

[98] A method for the prophylaxis and/or treatment of a bipolar disorder comprising administering daily 0.1 to 0.8 mg of (S)—N-[2-(1,6,7,8-tetrahydro-2H-indeno[5,4-b]furan-8-yl)ethyl]propionamide (compound A) to the oral mucosa of a human in need thereof, wherein the AUC ratio of a metabolite of compound A (M-II) to compound A in an unchanged form after administration is not more than 20.

[99] The method of afore-mentioned [97], wherein the AUC ratio is not more than 10.

[100] The method of afore-mentioned [98], wherein the AUC ratio is not more than 10.

[101] The method of any of afore-mentioned [70] to [72], wherein the AUC ratio of (S)—N-[2-(1,6,7,8-tetrahydro-2H-indeno[5,4-b]furan-8-yl)ethyl]propionamide in an unchanged form, to a metabolite of (S)—N-[2-(1,6,7,8-tetrahydro-2H-indeno[5,4-b]furan-8-yl)ethyl]propionamide (M-II) after administration is not less than about 5-fold than that by oral administration.

[102] The method of any of the afore-mentioned [101], wherein the AUC ratio is not less than about 10-fold than that by oral administration.

[103] The method of any of the afore-mentioned [102], wherein the AUC ratio is not more than about 30-fold, preferably, not more than about 20-fold.

[104] The method of any of afore-mentioned [70] to [72], wherein the AUC ratio of a metabolite of (S)—N-[2-(1,6,7, 8-tetrahydro-2H-indeno[5,4-b]furan-8-yl)ethyl]propionamide (M-II) to (S)—N-[2-(1,6,7,8-tetrahydro-2H-indeno[5, 4-b]furan-8-yl)ethyl]propionamide in an unchanged form after administration is not more than 20.

[105] The method of afore-mentioned [104], wherein the AUC ratio is not more than about 10, more preferably, not more than about 5.

[106] The method of any of the afore-mentioned [70] to [72], wherein (S)—N-[2-(1,6,7,8-tetrahydro-2H-indeno[5,4-b]furan-8-yl)ethyl]propionamide is administered so that the bioavailability of (S)—N-[2-(1,6,7,8-tetrahydro-2H-indeno[5, 4-b]furan-8-yl)ethyl]propionamide is improved not less than about 10-fold than that by oral administration, more specifically, is improved within the range from not less than about 10-fold to not more than about 30-fold than that by oral administration.

[107] The method of any of afore-mentioned [70] to [72], and [101] to [106], wherein (S)—N-[2-(1,6,7,8-tetrahydro-2H-indeno[5,4-b]furan-8-yl)ethyl]propionamide is administered so that the average Tmax value of plasma level of (S)—N-[2-(1,6,7,8-tetrahydro-2H-indeno[5,4-b]furan-O-yl)ethyl]propionamide after administration is not more than about 0.4 hrs, preferably, not more than about 0.3 hrs, and more preferably, not more than about 0.25 hrs.

[108] The method of any of afore-mentioned [70] to [72], and [101] to [107], wherein (S)—N-[2-(1,6,7,8-tetrahydro-2H-indeno[5,4-b]furan-8-yl)ethyl]propionamide is administered so that the coefficient of variation (CV) of pharmacokinetic parameters including Cmax and AUC of (S)—N-[2-(1,6,7,8-tetrahydro-2H-indeno[5,4-b]furan-8-yl)ethyl]propionamide after administration is not more than about 45%, preferably, not more than about 35%, and more preferably, not more than about 30%.

[109] The method of any of the above-mentioned [70] to [72] and [101] to [108], wherein the bipolar disorder is bipolar disorder I.

[110] The method of the above-mentioned [109], wherein the prophylaxis and/or treatment of a bipolar disorder is a treatment of a depression symptom associated with the bipolar disorder or maintenance of a remission phase of the bipolar disorder.

[111] A drug for the prophylaxis and/or treatment of a bipolar disorder comprising daily 0.1 mg of (S)—N-[2-(1,6,7,8-tetrahydro-2H-indeno[5,4-b]furan-8-yl)ethyl]propionamide (compound A) to be administered to the oral mucosa of a human in need thereof, wherein in the fasting state, Cmax for compound A falls within the range of about 0.43 to about 3.13 ng/ml and AUC (0-tlgc) for compound A falls within the range of about 0.48 to about 2.26 ng·hr/ml.

[112] The drug of the above-mentioned [111], wherein the oral-mucosal administration is sublingual administration or buccal administration.

[113] The drug of any of the above-mentioned [111] and [112], wherein the bipolar disorder is bipolar disorder I.

[114] The drug of any of the above-mentioned [111] to [113], wherein the prophylaxis and/or treatment of a bipolar disorder is a treatment of a depression symptom associated with the bipolar disorder or maintenance of a remission phase of the bipolar disorder.

[115] The drug of the above-mentioned [111], wherein in the fasting state, Cmax for compound A falls within the range of about 0.66 to about 2.05 ng/ml and AUC (0-tlqc) for compound A falls within the range of about 0.67 to about 1.62 ng·hr/ml.

[116] The drug of the above-mentioned [115], wherein the oral-mucosal administration is sublingual administration or buccal administration.

[117] The drug of any of the above-mentioned [115] and [116], wherein the bipolar disorder is bipolar disorder I.

[118] The drug of any of the above-mentioned [115] to [117], wherein the prophylaxis and/or treatment of a bipolar disor-

[119] A drug for the prophylaxis and/or treatment of a bipolar disorder comprising daily 0.4 mg of (S)—N-[2-(1,6,7,8-tetrahydro-2H-indeno[5,4-b]furan-8-yl)ethyl]propionamide (compound A) to be administered to the oral mucosa of a human in need thereof, wherein in the fasting state, Cmax for compound A falls within the range of about 2.04 to about 6.89 ng/ml and AUC (0-tlqc) for compound A falls within the range of about 1.52 to about 6.68 ng·hr/ml.
[120] The drug of the above-mentioned [119], wherein the oral-mucosal administration is sublingual administration or buccal administration.
[121] The drug of any of the above-mentioned [119] and [120], wherein the bipolar disorder is bipolar disorder I.
[122] The drug of any of the above-mentioned [119] to [121], wherein the prophylaxis and/or treatment of a bipolar disorder is a treatment of a depression symptom associated with the bipolar disorder or maintenance of a remission phase of the bipolar disorder.
[123] The drug of the above-mentioned [119], wherein in the fasting state, Cmax for compound A falls within the range of about 2.54 to about 5.54 ng/ml and AUG (0-tlqc) for compound A falls within the range of about 1.98 to about 5.12 ng·hr/ml.
[124] The drug of the above-mentioned [123], wherein the oral-mucosal administration is sublingual administration or buccal administration.
[125] The drug of any of the above-mentioned [123] and [124], wherein the bipolar disorder is bipolar disorder I.
[126] The drug of any of the above-mentioned [123] to [125], wherein the prophylaxis and/or treatment of a bipolar disorder is a treatment of a depression symptom associated with the bipolar disorder or maintenance of a remission phase of the bipolar disorder.
[127] A drug for the prophylaxis and/or treatment of a bipolar disorder comprising daily 0.8 mg of (S)—N-[2-(1,6,7,8-tetrahydro-2H-indeno[5,4-b]furan-8-yl)ethyl]propionamide (compound A) to be administered to the oral mucosa of a human in need thereof, wherein in the fasting state, Cmax for compound A falls within the range of about 3.63 to about 14.06 ng/ml and AUC (0-tlqc) for compound A falls within the range of about 2.48 to about 14.43 ng·hr/ml.
[128] The drug of the above-mentioned [127], wherein the oral-mucosal administration is sublingual administration or buccal administration.
[129] The drug of any of the above-mentioned [127] and [128], wherein the bipolar disorder is bipolar disorder I.
[130] The drug of any of the above-mentioned [127] to [129], wherein the prophylaxis and/or treatment of a bipolar disorder is a treatment of a depression symptom associated with the bipolar disorder or maintenance of a remission phase of the bipolar disorder.
[131] The drug of the above-mentioned [127], wherein in the fasting state, Cmax for compound A falls within the range of about 4.85 to about 10.54 ng/ml and AUC (0-tlqc) for compound A falls within the range of 3.60 to about 9.91 ng·hr/ml.
[132] The drug of the above-mentioned [131], wherein the oral-mucosal administration is sublingual administration or buccal administration.
[133] The drug of any of the above-mentioned [131] and [132], wherein the bipolar disorder is bipolar disorder I.
[134] The drug of any of the above-mentioned [131] to [133], wherein the prophylaxis and/or treatment of a bipolar disorder is a treatment of a depression symptom associated with the bipolar disorder or maintenance of a remission phase of the bipolar disorder.
[135] (S)—N-[2-(1,6,7,8-tetrahydro-2H-indeno[5,4-b]furan-8-yl)ethyl]propionamide (compound A) for the prophylaxis and/or treatment of a bipolar disorder, wherein 1) daily 0.1 mg of compound A is administered to the oral mucosa of a human in need thereof, and 2) in the fasting state, Cmax for compound A falls within the range of about 0.43 to about 3.13 ng/ml and AUC (0-tlqc) for compound A falls within the range of about 0.48 to about 2.26 ng·hr/ml.
[136] The (S)—N-[2-(1,6,7,8-tetrahydro-2H-indeno[5,4-b]furan-8-yl)ethyl]propionamide (compound A) of the above-mentioned [135], wherein the oral-mucosal administration is sublingual administration or buccal administration.
[137] The (S)—N-[2-(1,6,7,8-tetrahydro-2H-indeno[5,4-b]furan-8-yl)ethyl]propionamide (compound A) of any of the above-mentioned [135] and [136], wherein the bipolar disorder is bipolar disorder I.
[138] The (S)—N-[2-(1,6,7,8-tetrahydro-2H-indeno[5,4-b]furan-8-yl)ethyl]propionamide (compound A) of any of the above-mentioned [135] to [137], wherein the prophylaxis and/or treatment of a bipolar disorder is a treatment of a depression symptom associated with the bipolar disorder or maintenance of a remission phase of the bipolar disorder.
[139] The (S)—N-[2-(1,6,7,8-tetrahydro-2H-indeno[5,4-b]furan-8-yl)ethyl]propionamide (compound A) of the above-mentioned [135], wherein in the fasting state, Cmax for compound A falls within the range of about 0.66 to about 2.05 ng/ml and AUC (0-tlqc) for compound A falls within the range of about 0.67 to about 1.62 ng·hr/ml.
[140] The (S)—N-[2-(1,6,7,8-tetrahydro-2H-indeno[5,4-b]furan-8-yl)ethyl]propionamide (compound A) of the above-mentioned [139], wherein the oral-mucosal administration is sublingual administration or buccal administration.
[141] The (S)—N-[2-(1,6,7,8-tetrahydro-2H-indeno[5,4-b]furan-8-yl)ethyl]propionamide (compound A) of any of the above-mentioned [139] and [140], wherein the bipolar disorder is bipolar disorder I.
[142] The (S)—N-[2-(1,6,7,8-tetrahydro-2H-indeno[5,4-b]furan-8-yl)ethyl]propionamide (compound A) of any of the above-mentioned [139] to [141], wherein the prophylaxis and/or treatment of a bipolar disorder is a treatment of a depression symptom associated with the bipolar disorder or maintenance of a remission phase of the bipolar disorder.
[143] (S)—N-[2-(1,6,7,8-tetrahydro-2H-indeno[5,4-b]furan-8-yl)ethyl]propionamide (compound A) for the prophylaxis and/or treatment of a bipolar disorder, wherein 1) daily 0.4 mg of compound A is administered to the oral mucosa of a human in need thereof, and 2) in the fasting state, Cmax for compound A falls within the range of about 2.04 to about 6.89 ng/ml and AUC (0-tlqc) for compound A falls within the range of about 1.52 to about 6.68 ng·hr/ml.
[144] The (S)—N-[2-(1,6,7,8-tetrahydro-2H-indeno[5,4-b]furan-8-yl)ethyl]propionamide (compound A) of the above-mentioned [143], wherein the oral-mucosal administration is sublingual administration or buccal administration.
[145] The (S)—N-[2-(1,6,7,8-tetrahydro-2H-indeno[5,4-b]furan-8-yl)ethyl]propionamide (compound A) of any of the above-mentioned [143] and [144], wherein the bipolar disorder is bipolar disorder I.
[146] The (S)—N-[2-(1,6,7,8-tetrahydro-2H-indeno[5,4-b]furan-8-yl)ethyl]propionamide (compound A) of any of the above-mentioned [143] to [145], wherein the prophylaxis and/or treatment of a bipolar disorder is a treatment of a depression symptom associated with the bipolar disorder or maintenance of a remission phase of the bipolar disorder.

[147] The (S)—N-[2-(1,6,7,8-tetrahydro-2H-indeno[5,4-b]furan-8-yl)ethyl]propionamide (compound A) of the above-mentioned [143], wherein in the fasting state, Cmax for compound A falls within the range of about 2.54 to about 5.54 ng/ml and AUC (0-tlqc) for compound A falls within the range of about 1.98 to about 5.12 ng·hr/ml.

[148] The (S)—N-[2-(1,6,7,8-tetrahydro-2H-indeno[5,4-b]furan-8-yl)ethyl]propionamide (compound A) of the above-mentioned [147], wherein the oral-mucosal administration is sublingual administration or buccal administration.

[149] The (S)—N-[2-(1,6,7,8-tetrahydro-2H-indeno[5,4-b]furan-8-yl)ethyl]propionamide (compound A) of any of the above-mentioned [147] and [148], wherein the bipolar disorder is bipolar disorder I.

[150] The (S)—N-[2-(1,6,7,8-tetrahydro-2H-indeno[5,4-b]furan-8-yl)ethyl]propionamide (compound A) of any of the above-mentioned [147] to [149], wherein the prophylaxis and/or treatment of a bipolar disorder is a treatment of a depression symptom associated with the bipolar disorder or maintenance of a remission phase of the bipolar disorder.

[151] (S)—N-[2-(1,6,7,8-tetrahydro-2H-indeno[5,4-b]furan-8-yl)ethyl]propionamide (compound A) for the prophylaxis and/or treatment of a bipolar disorder, wherein 1) daily 0.8 mg of compound A is administered to the oral mucosa of a human in need thereof, and 2) in the fasting state, Cmax for compound A falls within the range of about 3.63 to about 14.06 ng/ml and AUC (0-tlqc) for compound A falls within the range of about 2.48 to about 14.43 ng·hr/ml.

[152] The (S)—N-[2-(1,6,7,8-tetrahydro-2H-indeno[5,4-b]furan-8-yl)ethyl]propionamide (compound A) of the above-mentioned [151], wherein the oral-mucosal administration is sublingual administration or buccal administration.

[153] The (S)—N-[2-(1,6,7,8-tetrahydro-2H-indeno[5,4-b]furan-8-yl)ethyl]propionamide (compound A) of any of the above-mentioned [151] and [152], wherein the bipolar disorder is bipolar disorder I.

[154] The (S)—N-[2-(1,6,7,8-tetrahydro-2H-indeno[5,4-b]furan-8-yl)ethyl]propionamide (compound A) of any of the above-mentioned [151] to [153], wherein the prophylaxis and/or treatment of a bipolar disorder is a treatment of a depression symptom associated with the bipolar disorder or maintenance of a remission phase of the bipolar disorder.

[155] The (S)—N-[2-(1,6,7,8-tetrahydro-2H-indeno[5,4-b]furan-8-yl)ethyl]propionamide (compound A) of the above-mentioned [151], wherein in the fasting state, Cmax for compound A falls within the range of about 4.85 to about 10.54 ng/ml and AUC (0-tlqc) for compound A falls within the range of 3.60 to about 9.91 ng·hr/ml.

[156] The (S)—N-[2-(1,6,7,8-tetrahydro-2H-indeno[5,4-b]furan-8-yl)ethyl]propionamide (compound A) of the above-mentioned [155], wherein the oral-mucosal administration is sublingual administration or buccal administration.

[157] The (S)—N-[2-(1,6,7,8-tetrahydro-2H-indeno[5,4-b]furan-8-yl)ethyl]propionamide (compound A) of any of the above-mentioned [155] and [156], wherein the bipolar disorder is bipolar disorder I.

[158] The (S)—N-[2-(1,6,7,8-tetrahydro-2H-indeno[5,4-b]furan-8-yl)ethyl]propionamide (compound A) of any of the above-mentioned [155] to [157], wherein the prophylaxis and/or treatment of a bipolar disorder is a treatment of a depression symptom associated with the bipolar disorder or maintenance of a remission phase of the bipolar disorder.

DETAILED DESCRIPTION OF THE INVENTION

Effect of the Invention

According to the present invention, a rapidly disintegrating preparation superior in the disintegration property, a preparation with improved medicament bioavailability and production methods thereof and the like can be provided.

The rapidly disintegrating preparations [1] to [7] of the present invention contain a medicament in granules, and a disintegrant as an extragranule component. Even when a medicament (e.g., compound A etc.) with poor compatibility with the disintegrant is to be used, therefore, an influence of the disintegrant on the medicament can be reduced, thus improving the stability of the medicament.

The rapidly disintegrating preparation of the present invention can improve disintegration property by enclosing a component that prevents disintegration (e.g., masking agent, binder etc.) in granules. In addition, it can achieve high disintegration property by ensuring the invasion route of water into the preparation by coating the component that prevents disintegration with sugar or sugar alcohol. Moreover, in the rapidly disintegrating preparation of the present invention, a medicament is coated with sugar or sugar alcohol. Therefore, the dissolution property of the medicament from the preparation can be improved even when the medicament has high surface hydrophobicity, by altering the surface to be hydrophilic.

The rapidly disintegrating preparation of the present invention can achieve both the good disintegration property and the good preparation hardness.

Among the rapidly disintegrating preparations [1] to [7] of the present invention, the rapidly disintegrating preparations [5] to [7] for oral-mucosal absorption of the present invention are expected to provide an immediate effect by absorption of the medicament from the oral mucosa.

The rapidly disintegrating preparation for oral-mucosal absorption of the present invention can improve bioavailability by increasing the blood concentration of a medicament (e.g., compound A etc.) susceptible to a first pass effect by oral administration. In addition, the rapidly disintegrating preparation for oral-mucosal absorption of the present invention can suppress inconsistent absorption of such medicaments, and further, inconsistent effectiveness as medicaments. Moreover, the rapidly disintegrating preparation for oral-mucosal absorption of the present invention can afford a low dose medicament and a compact preparation based on the improved medicament bioavailability.

According to the production method of the present invention, the rapidly disintegrating preparations [1] to [7] of the present invention having the above-mentioned effects can be produced.

DESCRIPTION OF EMBODIMENTS

Formulation

A Rapidly Disintegrating Preparation

Figure 1:
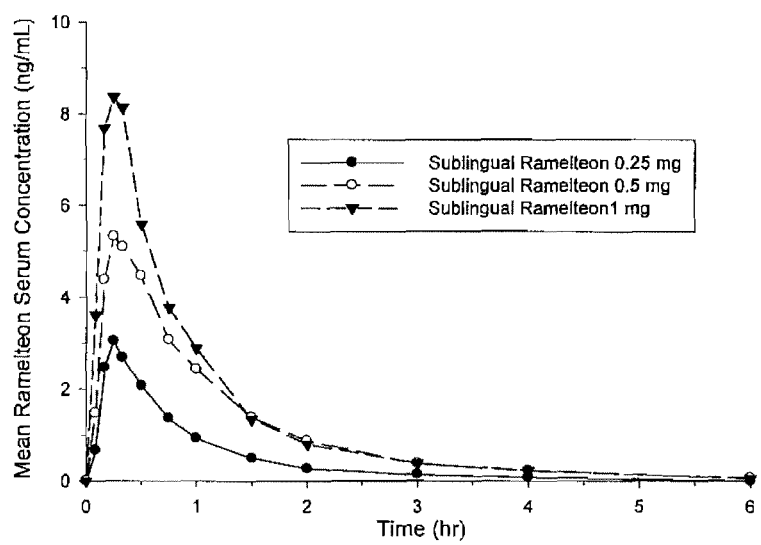
FIG. 1 demonstrates the mean serum concentration of compound A after oral-mucosal delivery at different concentrations.

The rapidly disintegrating preparation of the present invention is explained in detail in the following.

The rapidly disintegrating preparation of the present invention contains granules comprising a medicament coated with a coating layer containing sugar or sugar alcohol, and a disintegrant.

While the medicament to be used in the present invention is not particularly limited, for example, antipyretic analgesic antiphlogistic drugs, antipsychotic drugs, antianxiety drugs, antidepressant drugs, sedative-hypnotic drugs, gastrointestinal drugs, antacid drugs, antitussive expectorant drugs, antihypertensive agents, drugs for diabetes, drugs for osteoporosis, skeleton muscle relaxants, anti-cancer agents and the like can be used.

In the rapidly disintegrating preparation of the present invention, the content of the medicament is generally 0.03-50 wt %, preferably 0.03-20 wt %, more preferably 0.03-3 wt %, relative to the total weight of the preparation.

The rapidly disintegrating preparation of the present invention contains a disintegrant as an extragranule component, and therefore, an influence of the disintegrant on the medicament can be reduced even when a medicament having poor compatibility with the disintegrant is used, and the medicament stability can be improved. Thus, the present invention is particularly effective when a medicament having poor compatibility with the disintegrant (e.g. compound A, etc) is used as a medicament.

Compound A is a known therapeutic agent for sleep disorders, which is disclosed in U.S. Pat. No. 6,034,239 and the like, and can be produced by a known method such as the method described in this document and the like.

In the rapidly disintegrating preparation of the present invention, an excipient is contained in granules comprising a medicament coated with a coating layer containing sugar or sugar alcohol.

Examples of the excipient include starches such as corn starch and the like; sugar or sugar alcohols such as lactose, fructose, glucose, mannitol (e.g., D-mannitol), sorbitol (e.g., D-sorbitol), erythritol (e.g., D-erythritol), sucrose and the like: anhydrous calcium phosphate, microcrystalline cellulose, micromicrocrystalline cellulose, powdered glycyrrhiza, sodium hydrogen carbonate, calcium phosphate, calcium sulfate, calcium carbonate, precipitated calcium carbonate, calcium silicate and the like, and corn starch, D-mannitol and microcrystalline cellulose are preferable.

The content of the excipient is generally 13-94 wt %, preferably 54-94 wt %, more preferably 81-93 wt %, relative to the total weight of the preparation.

The rapidly disintegrating preparation of the present invention may further contain an additive, where necessary, in the granules comprising a medicament.

Examples of the additive optionally contained in the granules comprising a medicament include binder, masking agent, solubilizer and the like, which may be used in combination where necessary.

Examples of the binder include starches such as potato starch, wheat starch, rice starch, partly pregelatinized starch, pregelatinized starch, porous starch and the like, hydroxypropylcellulose, hydroxypropylmethylcellulose, polyvinylpyrrolidone, gelatin, starch, gum arabic powder, tragacanth, carmellose, sodium alginate, pullulan, glycerol and the like, and partly pregelatinized starch, hydroxypropylcellulose and pregelatinized starch are preferable.

The content of the binder is generally 0.5-20 wt %, preferably 0.5-15 wt %, more preferably 1-10 wt %, relative to the total weight of the preparation.

Examples of the masking agent include various flavoring agents (thaumatin, sucralose, saccharin, aspartame, xylitol, citric acid, L-sodium glutamate etc.), various receptor antagonists (BENECOAT, sodium chloride etc.), various cation channel antagonists (L-arginine etc.), various clathration agents ($\alpha$-cyclodextrin, $\beta$-cyclodextrin etc.), various flavors (strawberry flavor, mint flavor, orange flavor, vanillin etc.) and the like. Two or more thereof may be used in combination where necessary.

The content of the masking agent is generally 0.01-10 wt %, preferably 0.01-5 wt %, more preferably 0.01-1 wt %, relative to the total weight of the preparation.

Examples of the solubilizer include various aqueous solvents (polyethylene glycol, propylene glycol, glycerol etc.), various clathration agents ($\alpha$-cyclodextrin, cyclodextrin etc.), various surfactants (sodium lauryl sulfate, polysorbate 80, polyoxyethylene(160)polyoxypropylene(30)glycol etc.) and the like. Two or more thereof may be used in combination where necessary.

The content of the solubilizer is generally not more than 20 wt %, preferably not more than 15 wt %, more preferably not more than 10 wt %, relative to the total weight of the preparation.

In the rapidly disintegrating preparation of the present invention, disintegration property can be improved by including a component that prevents disintegration (e.g., masking agent, binder, solubilizer etc.) in granules. In addition, as mentioned below, the preparation can achieve high disintegration property by ensuring the invasion route of water into the preparation by coating the component that prevents disintegration with sugar or sugar alcohol.

The rapidly disintegrating preparation of the present invention contains sugar or sugar alcohol in a coating layer formed on the granules comprising a medicament.

Examples of the sugar or sugar alcohol include lactose, fructose, glucose, mannitol (e.g., D-mannitol), sorbitol (e.g., D-sorbitol), erythritol (e.g., D-erythritol), sucrose and the like, and D-mannitol is preferable.

The preparation can achieve high disintegration property by ensuring the invasion route of water into the preparation by coating the granules comprising a medicament with sugar or sugar alcohol. In addition, the dissolution property of the medicament from the preparation can be improved.

The content of the sugar contained in the coating layer is generally 5-20 wt %, preferably 5-15 wt %, more preferably 5-10 wt %, relative to the total weight of the preparation.

The content of the sugar alcohol contained in the coating layer is generally 5-20 wt %, preferably 5-15 wt %, more preferably 5-10 wt %, relative to the total weight of the preparation.

The content of the sugar and sugar alcohol contained in is the coating layer is generally 5-20 wt %, preferably 5-15 wt %, more preferably 5-10 wt %, relative to the total weight of the preparation.

The rapidly disintegrating preparation of the present invention may further contain an additive in the coating layer as necessary.

Examples of the additive optionally contained in the coating layer include excipient, disintegrant and the like, which may be used in combination as necessary.

Examples of the excipient include starches such as corn starch and the like; anhydrous calcium phosphate, microcrystalline cellulose, micromicrocrystalline cellulose, powdered glycyrrhiza, sodium hydrogen carbonate, calcium phosphate, calcium sulfate, calcium carbonate, precipitated calcium carbonate, calcium silicate and the like, and corn starch and microcrystalline cellulose are preferable.

Examples of the disintegrant include amino acid, starch, corn starch, carmellose, carmellose sodium, carmellose calcium, croscarmellose sodium, crospovidone, low-substituted hydroxypropylcellulose, hydroxypropyl starch, sodium carboxymethyl starch and the like, and crospovidone and carmellose are preferable.

In the rapidly disintegrating preparation of the present invention, the average particle size of the "granules comprising a medicament coated with a coating layer containing sugar or sugar alcohol" is generally 50 µm-500 µm, preferably 50 µm-355 µm, more preferably 50 µm-150 µm.

In the present specification, the average particle size is a value measured by a laser diffraction particle size analyzer, SYMPATEC: HELOS&RODOS and the like.

In the rapidly disintegrating preparation of the present invention, examples of the disintegrant contained as an extragranule component include amino acid, starch, corn starch, carmellose, carmellose sodium, carmellose calcium, croscarmellose sodium, crospovidone, low-substituted hydroxypropylcellulose, hydroxypropyl starch, sodium carboxymethyl starch and the like, and crospovidone and carmellose are preferable.

The content of the disintegrant is generally 0.5-15 wt %, preferably 1-10 wt %, more preferably 2-5 wt %, relative to the total weight of the preparation.

In the rapidly disintegrating preparation of the present invention, examples of the lubricant optionally contained as an extragranule component include magnesium stearate, stearic acid, calcium stearate, talc (purified talc), sucrose esters of fatty acid, sodium stearyl fumarate and the like, and sodium stearyl fumarate is preferable.

The content of the lubricant is generally 0.5-2 wt %, preferably 0.5-1.5 wt %, more preferably 0.5-1 wt %, relative to the total weight of the preparation.

The rapidly disintegrating preparation of the present invention may further contain an additive as an extragranule component where necessary.

Examples of the additive include masking agent, solubilizer and the like, explained above, which may be used in combination where necessary.

The rapidly disintegrating preparation of the present invention is not only useful as a so-called "orally disintegratable preparation" aiming at oral administration of a medicament, but also preferable as a preparation for oral-mucosal absorption (particularly, sublingual preparation, buccal preparation).

The rapidly disintegrating preparation for oral-mucosal absorption of the present invention can be expected to show immediate effect by absorption from the oral mucosa.

While the dosage foam of the rapidly disintegrating preparation of the present invention is not particularly limited, it is preferably a tablet.

When the rapidly disintegrating preparation of the present invention is a tablet, the weight of the preparation is preferably about 20-200 mg.

When the rapidly disintegrating preparation of the present invention is a tablet, the absolute hardness is generally not less than 1.0 N/mm$^2$, preferably not less than 1.5 N/mm$^2$, more preferably not less than 2.0 N/mm$^2$. When the rapidly disintegrating preparation of the present invention is a tablet, the absolute hardness is generally not more than 5.0 N/mm$^2$.

When the rapidly disintegrating preparation of the present invention is a tablet, the disintegration time is generally not more than 30 sec, preferably not more than 15 sec, more preferably not more than 10 sec. When the rapidly disintegrating preparation of the present invention is a tablet, the disintegration time is generally not less than 1 sec.

In the rapidly disintegrating preparation of the present invention, the disintegration property can be improved by including, in granules, a component that prevents disintegration, as described above. In addition, it can achieve high disintegration property by ensuring the invasion route of water into the preparation by coating the component that prevents disintegration with sugar or sugar alcohol. Therefore, even when the rapidly disintegrating preparation of the present invention is molded to have the above-mentioned high absolute hardness, it shows good disintegration property. Thus, the rapidly disintegrating preparation of the present invention can achieve both the good disintegration property and the good preparation hardness.

The rapidly disintegrating preparation of the present invention preferably shows a disintegration time of not more than 30 sec, and absolute hardness of not less than 1.0 N/mm$^2$.

The rapidly disintegrating preparation of the present invention can be produced by a method conventionally used in the pharmaceutical-technical field. For example, the preparation can be produced by the following production method of the rapidly disintegrating preparation of the present invention.

The production method of the rapidly disintegrating preparation of the present invention includes
step (1): producing granules comprising a medicament,
step (2): forming a coating layer containing sugar or sugar alcohol on the obtained granules, and
step (3): mixing the coated granules with a disintegrant and molding the mixture.

In steps (1)-(3), an additive may be further added as necessary. As the kind and amount of the "medicament", "sugar", "sugar alcohol", "disintegrant" and "additive" to be used in steps (1)-(3), those exemplified for the above-mentioned rapidly disintegrating preparation can be mentioned. As the particle size of the coated granules obtained in step (2), the range exemplified as the particle size of the "granules comprising a medicament coated with a coating layer containing sugar or sugar alcohol" of the above-mentioned rapidly disintegrating preparation can be mentioned.

The production of the granule in step (1) and formation of the coating layer in step (2) can also be carried out simultaneously.

For example, the preparation can be specifically produced as follows.

Sugar or sugar alcohol (e.g., D-mannitol etc.) is dissolved in a suitable solvent (e.g., water etc.) to give a coating solution.

A medicament (e.g., compound A etc.) and any additive (e.g., excipient such as D-mannitol, microcrystalline cellulose and the like, binder such as partly pregelatinized starch and the like etc.) are mixed to give a mixture. The obtained mixture is granulated while spraying the coating solution thereon, and dried to give a granulated powder (coated granules). The obtained granulated powder (coated granules) may be sieved as necessary.

The obtained coated granules, a disintegrant (e.g., crospovidone etc.) and any additive (e.g., lubricant such as sodium stearyl fumarate etc., and the like) are mixed to give a mixed powder. The obtained mixed powder is compression-molded to give a tablet.

Here, the mixing (including granulation, drying, sieving and the like) is carried out by using a preparation machine, for example, V-type mixer, tumbler mixer (TM-30, TM-15S; SHOWA KAGAKU KIKAI CO., LTD.: TM20-0-0; Suchiro Kakoki Co., Ltd.), high speed mixer granulator (FM-VG-10; POWREX CORPORATION), universal kneader (HATA IRON WORKS CO., LTD.), fluid bed dryer granulator (LAB-1, FD-3S, FD-3SN, FD-5S; POWREX CORPORATION), box type vacuum dryer (Kusuki Kikai Seisakusho), power mill grinding machine (P-3, SHOWA KAGAKU KIKAI CO., LTD.), centrifugation rolling granulator (CF-mini, CF-260, CF-360; Freund Corporation), dry type granulator, spray-drying granulator, rolling granulator (MP-10; POWREX CORPORATION) and the like.

Coating is carried out by using, for example, a preparation machine, for example, centrifugation rolling granulator (CF-mini, CF-260, CF-360; Freund Corporation), rolling granulator (MP-10; POWREX CORPORATION), general fluidized bed coater, wurster-type coater and the like.

Compression molding is carried out by using, for example, single punch tableting machine (Kikusui Seisakusho Ltd.), rotary tableting machine (AQUARIUS 36K, AQUARIUS 2L; Kikusui Seisakusho Ltd.), AUTOGRAPH (AG-5000B, SHIMADZU Corporation) and the like, and by punching generally at a pressure of 1-30 kN.

Formulation: A Preparation for Oral-Mucosal Absorption of Compound A

The rapidly disintegrating preparation for oral-mucosal absorption of the present invention is particularly effective when a medicament (e.g., compound A etc.) susceptible to a first pass metabolism effect when administered orally is used. The rapidly disintegrating preparation for oral-mucosal absorption of the present invention can improve bioavailability by increasing the blood concentration of such medicament. In addition, the rapidly disintegrating preparation for oral-mucosal absorption of the present invention can suppress inconsistent absorption of such medicaments, and further, inconsistent effectiveness as medicaments. Moreover, the rapidly disintegrating preparation for oral-mucosal absorption of the present invention can afford a low dose medicament with the potential for fewer side effects when it is used for the treatment of a bipolar disorder, such as residual daytime sleepiness and/or fatigue, and a compact preparation based on the improved medicament bioavailability.

When compound A is particularly used as a medicament, the rapidly disintegrating preparation for oral-mucosal absorption of the present invention shows an effect in that the ratio of the medicament in an unchanged form to a metabolite of the medicament after transfer into blood is higher than that by oral administration. In addition, the rapidly disintegrating preparation for oral-mucosal absorption of the present invention shows not less than about 10-fold improved bioavailability of compound A, as compared to that by oral administration.

i. Preparation (A)

That is, the present invention also relates to a preparation for oral-mucosal absorption containing compound A as a medicament; which shows a higher ratio of the medicament in an unchanged form and a metabolite of the medicament, particularly M-II, after transfer into blood than that by oral administration (preparations [9] to [11], [17] and [18]) (hereinafter sometimes to be abbreviated as preparation (A) of the present invention).

When the dosage form of preparation (A) is a tablet, the disintegration time is preferably not more than 30 sec. When the dosage form in preparation (A) is a tablet, more preferably, the disintegration time is not more than 30 sec, and the absolute hardness is not less than 1.0 N/mm$^2$.

The aforementioned preparations [5] to [7] are also encompassed in the "preparation (A)".

ii. Preparation (B) and Bioavailability

The present invention also relates to a preparation for oral-mucosal absorption, which contains compound A, and shows not less than about 10-fold improved bioavailability of compound A, as compared to that by oral administration (preparations [12] to [18]) (hereinafter sometimes to be abbreviated as preparation (B) of the present invention). Here, "about"

means 5% error range. The bioavailability is generally improved within the range of not more than about 30-fold, more specifically not more than about 25-fold. In other words, the bioavailability is improved within the range from not less than about 10-fold to not more than about 30-fold, more specifically, within the range from not less than about 10-fold to not more than 25-fold.

When the dosage form of preparation (B) is a tablet, preferably, the disintegration time is not more than 30 sec. When the dosage form in preparation (B) is a tablet, more preferably, the disintegration time is not more than 30 sec, and the absolute hardness is not less than 1.0 N/mm$^2$.

The aforementioned preparations [5] to [7] are also encompassed in the "preparation (B)".

Here, whether or not "bioavailability of compound A is improved not less than about 10-fold as compared to oral administration" is evaluated as follows.

Each preparation is administered intravenously, orally or oral-mucosally, the plasma concentration after lapse of each time period is measured, and the area under the plasma concentration time curve (AUC) is calculated according to the method known in this art. There are two kinds of AUC values. One is AUC(0-tlqc), and the other is AUC(0-inf). AUC(0-tlqc) is area under the serum concentration-time curve from time 0 to time of the last quantifiable concentration (tlqc), calculated using the linear trapezoidal rule. AUC(0-inf) is area under the serum concentration-time curve from time 0 to infinity, calculated as AUC(0-inf)=AUC(0-tlqc)+lqc/λz, where tlqc is the time of last quantifiable concentration, lqc is the last quantifiable concentration, and λz is terminal elimination rate constant, calculated as the negative of the slope of the log-linear regression of the natural logarithm concentration-time curve during the terminal phase. Both AUC values can be used for evaluation of improvement of bioavailability, but in principle, the evaluation thereof is made based on AUC(0-inf) value.

(a) Method A for Calculating Bioavailability Ratio

Bioavailability (BA) is calculated according to the following formula (absolute bioavailability).

BA (%)=((oral or oral-mucosal administration AUC/ dose in oral or oral-mucosal administration)/ (intravenous administration AUC/dose in intravenous administration))×100.

The ratio of the calculated BA by oral-mucosal administration relative to the calculated BA by oral administration (that is, BA by oral-mucosal administration/BA by oral administration) is calculated. This ratio is referred to as "BA ratio" (Method A).

In this case, when the "ratio of the BA by oral-mucosal administration relative to the BA by oral administration" (absolute BA ratio) is not less than 10, the preparation is evaluated to show "not less than about 10-fold improved bioavailability of compound A as compared to that by oral administration".

As for the test method, the examples of specific preparations to be subjected to a test, the below-mentioned Experimental Example 3 can be referred to. However, when a substantially similar evaluation is possible, the method is not limited to that of Experimental Example 3.

(b) Method B for Calculating Bioavailability Ratio

As for another evaluation method of bioavailability ratio, namely, "ratio of the BA by oral-mucosal administration relative to the BA by oral administration" here, one can calculate it according to the following formula (Method B; relative BA ratio).

Relative BA ratio=$A/B$×100

(wherein "A" means oral mucosal administration AUC/dose of compound A in the oral mucosal preparation administered to a human subject; and "B" means oral administration AUC/dose of compound A in the oral preparation administered to a human subject)

As for the test method, the examples of specific preparations to be subjected to a test, the below-mentioned Experimental Example 4 can be referred to. However, when a substantially similar evaluation is possible, the method is not limited to that of Experimental Example 4. The example demonstrates greater bioavailability of oral-mucosal administration compared to oral administration.

In this case, when the "ratio of the BA by oral-mucosal administration relative to the BA by oral administration" (relative BA ratio) is not less than 10, the preparation is evaluated to show "not less than about 10-fold improved bioavailability of compound A as compared to that by oral administration".

iii. Preparation C and Ratio of Medicament in Unchanged Form to Metabolite of Medicament The present invention also relates to a preparation for oral-mucosal absorption, which contains compound A and shows a higher ratio of a medicament in an unchanged form and a metabolite of the medicament after transfer into blood than that by oral administration (preparations [9] to [11]) (hereinafter sometimes to be abbreviated as preparation (C) of the present invention).

The "greater than the ratio" specifically means not less than about 5-fold, preferably not less than about 10-fold. It is generally not more than about 30-fold, more specifically not more than about 20-fold. Here, "about" means 5% error range.

When the dosage form of preparation (C) is a tablet, preferably, the disintegration time is not more than 30 sec. When the dosage form of preparation (C) is a tablet, more preferably, disintegration time is not more than 30 sec, and the absolute hardness is not less than 1.0 N/mm$^2$.

The aforementioned preparations [5] to [7] are also encompassed in the "preparation (C)".

Here, whether or not the "ratio of the medicament in an unchanged form and a metabolite of the medicament after transfer into blood is higher than that by oral administration" is evaluated as follows.

Each preparation is administered orally or oral-mucosally, the plasma concentration of both the unchanged form and metabolite after lapse of each time period is measured, and the area under the plasma concentration time curve (AUC) of the both is calculated according to the method known in this art. There are two kinds of AUC values. One is AUC(0-tlqc), and the other is AUC(0-inf). AUC(0-tlqc) is area under the serum concentration-time curve from time 0 to time of the last quantifiable concentration (tlqc), calculated using the linear trapezoidal rule. AUC(0-inf) is area under the serum concentration-time curve from time 0 to infinity, calculated as AUC (0-inf)=AUC(0-tlqc)+lqc/λz, where tlqc is the time of last quantifiable concentration, lqc is the last quantifiable concentration, and λz is terminal elimination rate constant, calculated as the negative of the slope of the log-linear regression of the natural logarithm concentration-time curve during the terminal phase.

Both AUC values can be used for evaluation of improvement of bioavailability, but in principle, the evaluation thereof is made based on AUC(0-inf) value.

The ratio of the unchanged form and metabolite, (i.e., AUC of unchanged form/AUC of metabolite) in each preparation is calculated.

In this case, when the ratio by oral-mucosal administration is higher than that by oral administration, it is evaluated "the ratio of a medicament in an unchanged form and a metabolite of the medicament after transfer into blood is higher than that by oral administration".

As for the test method, the examples of specific preparations to be subjected to a test, the below-mentioned Experimental Example 4 is referenced. However, when a substantially similar evaluation is possible, the method is not limited to that of Experimental Example 4. A person skilled in the art would not have expected the level of metabolite, especially, the specific metabolite M-II out of many existing metabolites of compound A, by oral-mucosal administration to be as low as demonstrated in this experiment.

While the dosage forms of preparation (A), preparation (B) and preparation (C) are not particularly limited as long as they can be administered from the oral mucosa. For example, tablet (e.g., sublingual tablet, buccal tablet), film, troche, solution, suspension, freeze-dried preparation, chewing gum, spray and the like can be mentioned. Among these, tablet is preferable.

As the kind and amount of "compound A", "masking agent", "sugar", "sugar alcohol" and "disintegrant" to be used for preparation (A), preparation (B) or preparation (C), those exemplified for the above-mentioned rapidly disintegrating preparation can be mentioned.

In the present specification, the absolute hardness is hardness per unit area, and is defined according to the following formula.

$$\text{absolute hardness (N/mm}^2\text{)=hardness (N)/(thickness (mm)×diameter (mm))}$$

In the present invention, the tablet hardness can be measured by a tablet hardness tester (TH-303 MP, Toyama Sangyo CO., LTD.).

In the present specification, the disintegration time is a value measured by a disintegration tester (ODT-101, Toyama Sangyo CO., LTD.) for orally rapidly disintegrating tablet.

Formulation: A Preparation for Oral-Mucosal Absorption of Compound A (2)

iv. Preparation D

The present invention also relates to a preparation for oral-mucosal absorption (preparations [37] to [59]) (hereinafter sometimes to be abbreviated as preparation (D) of the present invention).

As for preparation (D), in principle, definitions of the terms specifying each preparation [37] to [59] and concrete examples thereof can be referred to those exemplified for preparations (A) to (C) above.

Concerning preparations [37] to [39], "the AUC ratio of (S)—N-[2-(1,6,7,8-tetrahydro-2H-indeno[5,4-b]furan-8-yl)ethyl]propionamide in an unchanged form to a metabolite of (S)—N-[2-(1,6,7,8-tetrahydro-2H-indeno[5,4-b]furan-8-yl)ethyl]propionamide (M-II)" means the value calculated by the formula:

"AUC of (S)—N-[2-(1,6,7,8-tetrahydro-2H-indeno[5,4-b]furan-8-yl)ethyl]propionamide in unchanged form/AUC of a metabolite of (S)—N-[2-(1,6,7,8-tetrahydro-2H-indeno[5,4-b]furan-8-yl)ethyl]propionamide (M-II)".

Here, the term "AUC" and the calculation method thereof can be referred to those exemplified for the preparations (A) to (C) above.

The AUC ratio is not less than about 5-fold than that by oral administration, preferably, not less than about 10-fold than that by oral administration. In general, the AUC ratio is not more than about 30-fold than that by oral administration, more specifically, not more than about 25-fold than that by oral administration. Here, "about" means 5% error range.

As for the test method, the examples of specific preparations to be subjected to a test, the below-mentioned Experimental Example 4 can be referred to. However, when a substantially similar evaluation is possible, the method is not limited to that of Experimental Example 4.

Concerning preparations [40] and [41], the AUC ratio of a metabolite of (S)—N-[2-(1,6,7,8-tetrahydro-2H-indeno[5,4-b]furan-8-yl)ethyl]propionamide (M-II) to (S)—N-[2-(1,6,7,8-tetrahydro-2H-indeno[5,4-b]furan-8-yl)ethyl]propionamide in an unchanged form means the value calculated by the formula:

"AUC of a metabolite of (S)—N-[2-(1,6,7,8-tetrahydro-2H-indeno[5,4-b]furan-8-yl)ethyl]propionamide (M-II)/AUC of (S)—N-[2-(1,6,7,8-tetrahydro-2H-indeno[5,4-b]furan-8-yl)ethyl] propionamide in unchanged form".

Here, the term "AUC" and the calculation method thereof can be referred to those exemplified for the preparations (A) to (C) above.

As for the test method, the examples of specific preparations to be subjected to a test, the below-mentioned Experimental Example 4 can be referred to. However, when a substantially similar evaluation is possible, the method is not limited to that of Experimental Example 4.

The AUC ratio is not more than about 25, preferably, not more than about 10, and more preferably, not more than about 5. In general, the AUC ratio is not less than about 1. Here, "about" means 5% error range.

Concerning preparation [42], "the bioavailability of (S)—N-[2-(1,6,7,8-tetrahydro-2H-indeno[5,4-b]furan-8-yl)ethyl]propionamide" can be calculated according to the evaluation method (Method B) as explained for preparation (B) before.

As for the test method, the examples of specific preparations to be subjected to a test, the below-mentioned Experimental Example 4 can be referred to. However, when a substantially similar evaluation is possible, the method is not limited to that of Experimental Example 4.

The bioavailability is not less than about 10-fold improved, as compared to that by oral administration. Here, "about" means 5% error range. In general, the bioavailability is improved within the range from not less than about 10-fold to not more than about 30-fold, more specifically, within the range from not less than about 10-fold to not more than about 25-fold than that by oral administration.

Concerning preparations [43] and [44], in the term of "Tmax value of plasma level of (S)—N-[2-(1,6,7,8-tetrahydro-2H-indeno[5,4-b]furan-8-yl)ethyl]propionamide after administration to a human", Tmax means time to reach Cmax, wherein Cmax means maximum observed serum concentration, after a preparation is administered to a human.

As for the test method, the examples of specific preparations to be subjected to a test, the below-mentioned Experimental Example 4 can be referred to. However, when a substantially similar evaluation is possible, the method is not limited to that of Experimental Example 4.

The average Tmax value is not more than about 0.4 hrs, preferably, not more than about 0.3 hrs, and more preferably, not more than about 0.25 hrs.

Concerning preparations [45] and [46], in the term of "the individual variability of pharmacokinetic parameters including Cmax and AUC of (S)—N-[2-(1,6,7,8-tetrahydro-2H-indeno[5,4-b]furan-8-yl)ethyl]propionamide (unchanged form) after administration to a human" is expressed in the term of "coefficient of variation (%)" which is calculated by the formula:

standard deviation/mean value for each target pharmacokinetic parameter×100

As for the test method, the examples of specific preparations to be subjected to a test, the below-mentioned Experimental Example 4 can be referred to. However, when a substantially similar evaluation is possible, the method is not limited to that of Experimental Example 4.

Individual variability is not more than about 45%, more preferably, not more than about 35%, and most preferably, not more than about 30%. Here, "about" means 5% error range.

Dosage Forms

Preparations (A)-(D) can be produced, for example, according to the production method explained for "the rapidly disintegrating preparation of the present invention". Particularly, when the dosage form of preparations (A)-(D) is tablet, such production method is preferable. It is also possible to apply other techniques for orally disintegrating preparations.

When the dosage form of preparations (A)-(D) is film, the preparations can be produced according to a conventional method as follows. For example, the preparation can be produced by applying or spraying a coating solution (solution or suspension, solvent is, for example, purified water) containing a medicament, a film carrier, other film carriers used as necessary and the like to the surface of a support medium, and drying same (JP-B-3460538).

When the dosage form of preparations (A)-(D) is freeze-dried preparation, the preparation can be produced according to a conventional method as follows. For example, the preparation can be produced by mixing a medicament, a polymer, sugars and the like, and dissolving and lyophilizing them (Manufacturing Chemist, February 36 (1990)).

When the dosage form of preparations (A)-(D) is chewing gum, the preparation can be produced according to a conventional method as follows. For example, the preparation can be produced by adding a medicament, additive such as sweetener, flavor, colorant, softening agent, flavoring substance and the like to a gum base containing a resin for a gum base as a main component, wax, an emulsifier and a filler, uniformly kneading them in a kneader, and processing them into a plate form, a block foist and the like (JP-A-2009-136240).

When the dosage form of preparations (A)-(D) is troche, the preparation can be produced according to a general production method of tablets.

When the dosage form of preparations (A)-(D) is solution or suspension, the preparation can be produced according to a general production method of liquids.

When the dosage form of preparations (A)-(D) is spray, the preparation can be produced according to a general production method of spray.

The preparation of the present invention can be safely administered to a mammal (e.g., human, mouse, rat, rabbit, dog, cat, bovine, horse, swine, monkey), particularly human.

The dose of the preparation of the present invention varies depending on the subject of administration, administration route, disease and the like. For example, when a preparation for oral-mucosal absorption containing compound A as a medicament is administered to an adult, the dose of compound A is about 0.0002-about 0.02 mg/kg body weight, preferably about 0.0002-about 0.01 mg/kg body weight, more preferably about 0.0002-about 0.005 mg/kg body weight, most preferably about 0.0002-about 0.004 mg/kg body weight, which can be administered in one to several portions a day, preferably once a day. In other words, as mentioned later, the dose of compound A is 0.05-1.5 mg (preferably, 0.05-1.0 mg, more preferably, 0.1-1.0 mg, much more preferably, 0.1-0.8 mg and most preferably, 0.1 mg, 0.4 mg and 0.8 mg) a day, which can be administered once a day.

The solubility of compound A is about 0.2 mg/ml irrespective of pH. In order for this compound to be absorbed oral-mucossally, the compound should be dissolved in saliva first. When it is taken into consideration that the amount of saliva in the oral cavity is about 1 ml, the reduction of amount of compound A which the present invention brings in is quite advantageous from practical viewpoint.

According to the preparation of the present invention, as mentioned above, the dose of compound A can be reduced with keeping its efficacy. Therefore, if necessary, the size of the preparation can be made smaller. This feature would be also one of the advantages of the present invention.

Method of Use of Compound A: Prophylaxis and/or Treatment of a Bipolar Disorder

It is known that melatonin secretion decreases to cause disorders in the circadian rhythm in patients with bipolar disorders. Neuroscience Letters, 475: 169-173 (2010); Journal of Psychiatric Research, 44:69-74 (2010).

When compound A is administered oral-mucosally to a human subject, it is surprisingly observed that the pharmacokinetics (rapid onset and offset of action) of Compound A is quite similar to that of the endogenous melatonin, and with the characteristic pharmacokinetic profile, compound A can regulate the circadian rhythm, which is thought to be disturbed in bipolar patients, better than existing drugs indicated for a bipolar disorder. Thus, when oral-mucosally administered, compound A is expected to show superior effect on bipolar disease to existing drugs. In addition, this circadian rhythm regulating effect can also translate into better normalizing circadian rhythm and/or sleep/awake cycle in bipolar patients.

As mentioned above, the present invention provides a preparation showing superior absorption of compound A from the oral mucosa and improved bioavailability thereof and characteristic pharmacokinetic profile thereof. For example, when compound A is administered oral-mucosally, the variability of Cmax and AUC between different individuals is less than when the compound A is administered orally.

For example, in Table 4, the Cmax of unchanged Compound A and the Cmax of active metabolite M-II for sublingual administration are 4.74±1.52 and 4.18±1.26, respectively, with an unchanged/metabolite ratio of 1.13. In contrast, the corresponding unchanged/metabolite Cmax and ratio for oral administration are 4.76±5.19, 68.1±23.2 and 0.07. The related AUC(0-inf) unchanged/metabolite ratios for sublingual and oral administrations are 0.30 and 0.03, respectively. Accordingly, Table 4 demonstrates that a higher ratio of unchanged Compound A to metabolite is produced with sublingual administration over oral administration. Accordingly, it is believed that sublingual or buccal administration bypasses first-pass metabolism and, as a result, reduces the variability that exists among patients in the metabolism of Compound A. Hence, a more effective method for the prophylaxis and/or treatment of bipolar disorders, and a more effective drug for the prophylaxis and/or treatment of bipolar disorders are provided.

To be precise, by oral-mucosal administration of compound A to patients affected with bipolar disorders, the bipolar disorders can be prevented and/or treated. Specifically, such prophylaxis and/or treatment can be performed by appropriately administering compound A in the form of the preparation of the present invention (preparations (A) to (D)) to humans. For example, the various kinds of PK profiles mentioned in the methods [59] to [71] can be achieved by administering compound A to a human in the foams of preparations [37] to [58].

Here, the administration route of compound A is preferably sublingual administration or buccal administration, and sublingual administration is particularly preferable.

The sublingual and buccal administration is advantageous for providing a quick onset of therapy and a quick offset of therapy. This is in contrast to oral administration, in which onset and offset is slower due to gastro-intestinal transit time. When compared with oral administration, the sublingual and buccal administrations result in a lower ratio of the metabolite M-II to Compound A. By providing a quick offset, patients affected with bipolar disorders benefit from the effects of Compound A without experiencing prolonged sleepiness that can be associated with the presence of the metabolites.

It is believed that the quick onset/quick offset property of sublingual and buccal administrations parallel the effects of endogenous melatonin. In one embodiment, the formulation provides a therapeutic effect by achieving a blood level above a certain therapeutic level for a certain period of time. The duration and blood level should correspond to an endogenous melatonin level in a normal individual who does not suffer from bipolar disorder.

While the dose of compound A is as mentioned above, for administration as a sublingual tablet or a buccal tablet, for example, a tablet containing 0.05-1.5 mg (preferably, 0.05-1.0 mg, more preferably, 0.1-1.0 mg, much more preferably, 0.1-0.8 mg and most preferably, 0.1 mg, 0.4 mg and 0.8 mg) of compound A per tablet is preferably administered to patients, preferably, once per day.

As to the target disease, the invention is effective for bipolar disorders including bipolar disorder I, bipolar disorder II (recurrent major depressive episodes with hypomanic episodes) (296.89), and bipolar disorder not otherwise specified (296.80). The numbers in brackets after the listed diseases above refer to the classification code in Diagnostic and Statistical Manual of Mental Disorders, 4th Edition, published by the American Psychiatric Association (DSM-IV) and/or the International Classification of Diseases, 10th Edition (ICD-10). However, it should be understood that the invention is intended to be used in the treatment of diseases related or similar to those described in this classification coding system which, of course, may change over time as more is understood about these disorders. The invention is particularly effective in the treatment of bipolar disorder I. Specifically, it is effective for the "treatment of depression symptoms (particularly, acute depression symptoms) associated with bipolar disorder" and "maintenance of remission phase of bipolar disorder".

For the "prophylaxis and/or treatment of bipolar disorders by oral-mucosal administration of compound A", other medicaments for the prophylaxis and/or treatment of bipolar disorders may be used in combination. Such other medicaments for the prophylaxis and/or treatment of bipolar disorders to be used in combination with "compound A" (hereinafter referred to as "combination medicament") may include mood stabilizer (e.g. lithium, valproic acid, carbamazepine, lamotrigine, etc) and antipsychotics (e.g. quetiapine, olanzapine, etc), and a combination of one or more medicaments selected from them. In addition thereto, one or more SSRI (selective serotonin reuptake inhibitors) (e.g. fluvoxamine, paroxetine, escitalopram, fluoxetine, citalopram, etc) may also be administered in combination with "compound A" and the aforementioned "combination medicament".

The administration mode of the "combination medicament" is not particularly restricted, and it is sufficient that "compound A" and "combination medicament" be combined in administration. Examples of such administration mode include the following:

(1) administration of a single preparation obtained by simultaneously processing "compound A" and "combination medicament",
(2) simultaneous administration of two kinds of preparations of "compound A" and "combination medicament", which have been separately produced, by the same administration route,
(3) administration of two kinds of preparations of "compound A" and "combination medicament", which have been separately produced, by the same administration route in a staggered manner,
(4) simultaneous administration of two kinds of preparations of "compound A" and "combination medicament", which have been separately produced, by different administration routes,
(5) administration of two kinds of preparations of "compound A" and "combination medicament", which have been separately produced, by different administration routes in a staggered manner (e.g., administration in the order of "compound A" and "combination medicament", or in the reverse order) and the like.

The dosage of the "combination medicament" may be determined according to the dose clinically used, and can be appropriately selected depending on an administration subject, administration route, seriousness of the disease, combination, and the like.

The "combination medicament" can be administered in the same dosage form as clinically used or in a different dosage form suitable for this combination therapy.

EXAMPLES

The present invention is explained in more detail in the following by referring to Examples, which are not to be construed as limitative. The preparation additives (e.g., D-mannitol, microcrystalline cellulose, and the like) used in the following Examples and Comparative Examples were the Japanese Pharmacopoeia 15th Edition or Japanese Pharmaceutical Excipients 2003 compatible products.

Example 1

(1) D-Mannitol (PEARLITOL 50C, Roquette) (450.0 g) was dissolved in purified water (2550 g) to give a coating solution. Compound A (150.5 g), D-mannitol (3068 g), microcrystalline cellulose (CEOLUS PH-101, Asahi Kasei Corporation) (112.5 g), and partly pregelatinized starch (PCS, Asahi Kasei Corporation) (450.0 g) were uniformly mixed in a fluid bed dryer granulator (FD-5S, POWREX CORPORATION), granulated while spraying the coating solution (3000 g), and dried to give a granulated powder. A part of the obtained granulated powder was ground in a power mill grinding machine (P-3, SHOWA KAGAKU KIKAI CO., LTD.) using a 1.5 mmϕ punching screen to give a sieved powder.
(2) To the obtained sieved powder (1692 g) were added crospovidone (Kollidon CL-F, BASF) (90 g) and sodium stearyl fumarate (PRUV, JRS PHARMA) (18 g), and the mixture was mixed in a tumbler mixer (TM-30, SHOWA KAGAKU KIKAI CO., LTD.) to give a mixed powder.
(3) The mixed powder was tableted by a rotary tableting machine (AQUA 08242L2JI, Kikusui Seisakusho Ltd.) using a 4 mmϕ punch (tableting pressure: 4 kN, weight per tablet: 30 mg) to give a tablet.

Composition of Preparation (30 mg)

| | |
|---|---|
| compound A | 1.0 mg |
| D-mannitol (in granules) | 20.45 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Comparative Example 1

Polyethylene glycol 400 (PEG400) (Wako Pure Chemical Industries, Ltd.) (15 g) was dissolved in purified water (35 g) to give PEG400 solution. Compound A (12.5 mg) was added to PEG400 solution (50 ml), and the mixture was stirred and insonated, and filtered using a hydrophilic filter (0.45 μm). The obtained compound A solution was divided into small portions (1 ml each).

Composition of Preparation (1 ml)

| | |
|---|---|
| compound A | 0.25 mg |
| PEG400 | 300.0 mg |
| purified water | 700.0 mg |
| total | 1000.25 mg |

Comparative Example 2

(1) Hydroxypropylcellulose (HPC-L, NIPPON SODA CO., LTD.) (40 g) was dissolved in purified water (627 g) to give a binding solution. Compound A (2.5 g), lactose (DMV INTERNATIONAL) (1053.5 g), and corn starch (Japan Corn Starch Co., Ltd.) (160 g) were uniformly mixed in a fluid bed dryer granulator (MP-01, POWREX CORPORATION), granulated while spraying the binding solution (667 g), and dried to give a granulated powder. The obtained granules were sieved through a 16 mesh (aperture 1.0 mm) sieve to give a sieved powder.
(2) Corn starch (17 g) and magnesium stearate (5 g) were added to the obtained sieved powder (628 g) and mixed in a bag to give a mixed powder.
(3) The mixed powder was tableted by a rotary tableting machine (compact tableting machine, Kikusui Seisakusho Ltd.) by using a 4 mmϕ punch (tableting pressure: 7 kN, weight per tablet: 130 mg) to give a tablet (core tablet).
(4) Hydroxypropylmethylcellulose (TC-5R) (22.44 g) and Copovidone (4.5 g) were dissolved in purified water (198 g) and dispersed therein to give dispersion I. Titanium oxide (25 g) and yellow ferric oxide (0.5 g) were dispersed in purified water (450 g) to give dispersion II. Dispersion II was added to dispersion I, and the mixture was stirred to give a coating solution. The coating solution was sprayed on the core tablet obtained in (3) until the weight of the core tablet increased by 5 mg per tablet by using a coater (High Coater HC-LABO, Freund Corporation) to give a film-coated tablet having the following composition.

Composition of Preparation (135 mg)

| | |
|---|---|
| compound A | 0.25 mg |
| lactose | 105.35 mg |

| | |
|---|---|
| corn starch | 19.4 mg |
| hydroxypropylcellulose | 4.0 mg |
| magnesium stearate | 1.0 mg |
| hydroxypropylmethylcellulose | 3.74 mg |
| Copovidone | 0.75 mg |
| titanium oxide | 0.5 mg |
| yellow ferric oxide | 0.01 mg |
| total | 135 mg |

Example 2

(1) D-Mannitol (PEARITOL 50C, Roquette) (120 g) was dissolved in purified water (680 g) to give a coating solution. Compound A (10 g), D-mannitol (848 g), microcrystalline cellulose (CEOLUS PH-101, Asahi Kasei Corporation) (30 g), and partly pregelatinized starch (PCS, Asahi Kasei Corporation) (120 g) were uniformly mixed in a fluid bed dryer granulator (MP-01, POWREX CORPORATION), granulated while spraying a coating solution (800 g), and dried to give a granulated powder. The obtained granules were sieved through a 16 mesh (aperture 1.0 mm) sieve to give a sieved powder.

(2) The obtained sieved powder (28.2 g), crospovidone (Kollidon CL-F, BASF) (1.5 g) and sodium stearyl fumarate (0.3 g) were mixed in a glass bottle. The obtained mixture was tableted (tableting pressure: 3 KN/punch, tablet weight per tablet: 30 mg) by an AUTOGRAPH (AG-5000B, SHIMADZU Corporation) using a 4 mmφ punch to give a core tablet with the following composition.

Composition of Preparation (30 mg)

| | |
|---|---|
| compound A | 0.25 mg |
| D-mannitol (in granules) | 21.2 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Comparative Example 3

PEG400 (Wako Pure Chemical Industries, Ltd.) (60 g) was dissolved in purified water (110 g) to give PEG400 solution. Compound A (100.0 mg) was added to the PEG400 solution (100 ml), and the mixture was stirred and insonated, and filtered using a hydrophilic filter (0.45 μm). The obtained compound A solution was divided into small portions (1 ml each).

Composition of Preparation (1 ml)

| | |
|---|---|
| compound A | 1.0 mg |
| PEG400 | 352.9 mg |
| purified water | 647.1 mg |
| total | 1001 mg |

Comparative Example 4

(1) Hydroxypropylcellulose (HPC-L, NIPPON SODA CO., LTD.) (660 g) was dissolved in purified water (10230 g) to give a binding solution. Compound A (165.3 g), lactose (DMV INTERNATIONAL) (17260 g), and corn starch (Japan Corn Starch Co., Ltd.) (2640 g) were uniformly mixed in a fluid bed dryer granulator (FD-S2, POWREX CORPORATION), granulated while spraying a binding solution (10890 g), and dried to give a granulated powder. This granulation step was performed twice. A part of the obtained granulated powder was ground by a power mill grinding machine (P-3, SHOWA KAGAKU KIKAI CO., LTD.) using a 1.5 mmφ punching screen to give a sieved powder.

(2) Corn starch (1013 g) and magnesium stearate (298 g) were added to the obtained sieved powder (37430 g), and the mixture was mixed in a tumbler mixer (TM20-0-0, Suchiro Kakoki Co., Ltd.) to give a mixed powder.

(3) The mixed powder was tableted by a rotary tableting machine (AQUARIUS 36K, Kikusui Seisakusho Ltd.) by using a 7 mmφ punch (tableting pressure: 7 kN, weight per tablet: 130 mg) to give a tablet (core tablet).

(4) Hydroxypropylmethylcellulose (TC-5R, Shin-Etsu Chemical Co., Ltd.) (1548 g) and Copovidone (310.5 g) were dissolved in purified water (16150 g) and dispersed therein to give dispersion I. Titanium oxide (207 g) and yellow ferric oxide (4.14 g) were dispersed in purified water (1822 g) to give dispersion II. Dispersion II was added to dispersion I, and the mixture was stirred to give a coating solution. Using a coater (High Coater HCF-100N, Freund Corporation), the coating solution was sprayed on the core tablet obtained in (3) until the weight of the core tablet increased by 5 mg per tablet to give a film-coated tablet having the following composition.

Composition of Preparation (135 mg)

| | |
|---|---|
| compound A | 1.0 mg |
| lactose | 104.6 mg |
| corn starch | 19.4 mg |
| hydroxypropylcellulose | 4.0 mg |
| magnesium stearate | 1.0 mg |
| hydroxypropylmethylcellulose | 3.74 mg |
| Copovidone | 0.75 mg |
| titanium oxide | 0.5 mg |
| yellow ferric oxide | 0.01 mg |
| total | 135 mg |

Example 3

(1) D-mannitol (PEARLITOL 50C, Roquette) (120 g) was dissolved in purified water (680 g) to give a coating solution. Compound A (40 g), D-mannitol (818 g), microcrystalline cellulose (CEOLUS PH-101, Asahi Kasei Corporation) (30 g), and partly pregelatinized starch (PCS, Asahi Kasei Corporation) (120 g) were uniformly mixed in a fluid bed dryer granulator (MP-01, POWREX CORPORATION), granulated while spraying the coating solution (800 g), and dried to give a granulated powder. The obtained granules were sieved through a 16 mesh (aperture 1.0 mm) sieve to give a sieved powder.

(2) The obtained sieved powder (28.2 g), crospovidone (Kollidon CL-F, BASF) (1.5 g) and sodium stearyl fumarate (0.3 g) were mixed in a glass bottle. The obtained mixture was tableted (tableting pressure: 3 KN/punch, tablet weight per tablet: 30 mg) by an AUTOGRAPH (AG-5000B, SHIMADZU Corporation) by using a 4 mmφ punch to give a core tablet with the following composition.

Composition of Preparation (30 mg)

| | |
|---|---|
| compound A | 1.0 mg |
| D-mannitol (in granules) | 20.45 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Example 4

Compound A (5 g) and CMEC (20 g) were dissolved in acetone:ethanol=3:2 mixed solution (500 ml), and spray-dried by a spray dryer (Pulvis Mini Spray, YAMATO SCIENTIFIC CO., LTD.). The obtained solid dispersion powder was dried in vacuo at 40° C. for 16 hr. To the solid dispersion powder (0.5 g) was added D-mannitol (PEARLITOL 100SD, Roquette) (11.5 g) and mixed in a bottle. The obtained mixed powder was divided into small portions (120 mg each).
Composition of Preparation (120 mg)

| | |
|---|---|
| compound A | 1.0 mg |
| CMEC | 4.0 mg |
| D-mannitol | 115.0 mg |
| total | 120 mg |

Example 5

Hydroxypropyl-β-cyclodextrin (hereinafter sometimes referred to as HP-β-CyD) (KLEPTOSE HPB, Roquette) (75 g) was dissolved in purified water (422.5 g). Compound A (2.5 g) was dissolved in the obtained HP-β-CyD aqueous solution to give a coating solution. D-Mannitol (PEARLITOL 50C, Roquette) (200 g) and microcrystalline cellulose (CEOLUS PH-101, Asahi Kasei Corporation) (7.5 g) were uniformly mixed in a fluid bed dryer granulator (MP-01, POWREX CORPORATION), granulated while spraying the coating solution (500 g), and dried to give a granulated powder. The obtained granules were sieved through a 16 mesh (aperture 1.0 mm) sieve to give a sieved powder. The obtained sieved powder was divided into small portions (114 mg each).
Composition of Preparation (114 mg)

| | |
|---|---|
| compound A | 1.0 mg |
| HP-β-CyD | 30.0 mg |
| D-mannitol | 80.0 mg |
| microcrystalline cellulose | 3.0 mg |
| total | 114 mg |

Example 6

(1) D-Mannitol (PEARLITOL 50C, Roquette) (450 g) was dissolved in purified water (2550 g) to give a coating solution. Compound A (37.6 g), D-mannitol (3180 g), microcrystalline cellulose (CEOLUS PH-101, Asahi Kasei Corporation) (112.5 g), and partly pregelatinized starch (PCS, Asahi Kasei Corporation) (450 g) were uniformly mixed in a fluid bed dryer granulator (FD-5S, POWREX CORPORATION), granulated while spraying the coating solution (3000 g), and dried to give a granulated powder. A part of the obtained granulated powder was ground by a power mill grinding machine (P-3, SHOWA KAGAKU KIKAI CO., LTD.) using a 1.5 mmϕ punching screen to give a sieved powder.
(2) Crospovidone (Kollidon CL-F, BASF) (90 g) and sodium stearyl fumarate (18 g) were added to the obtained sieved powder (1692 g), and the mixture was mixed in a tumbler mixer (TM-15S, SHOWA KAGAKU KIKAI CO., LTD.) to give a mixed powder.
(3) The mixed powder was tableted by a rotary tableting machine (AQUARIUS 2L, Kikusui Seisakusho Ltd.) by using a 4 mmϕ punch (tableting pressure: 4 kN, weight per tablet: 30 mg) to give a core tablet with the following composition.
Composition of Preparation (30 mg)

| | |
|---|---|
| compound A | 0.25 mg |
| D-mannitol (in granules) | 21.2 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Example 7

(1) D-mannitol (PEARLITOL 50C, Roquette) (450 g) was dissolved in purified water (2550 g) to give a coating solution. Compound A (150.5 g), D-mannitol (3068 g), microcrystalline cellulose (CEOLUS PH-101, Asahi Kasei Corporation) (112.5 g), and partly pregelatinized starch (PCS, Asahi Kasei Corporation) (450 g) were uniformly mixed in a fluid bed dryer granulator (FD-5S, POWREX CORPORATION), granulated while spraying the coating solution (3000 g), and dried to give a granulated powder. A part of the obtained granulated powder was ground by a power mill grinding machine (P-3, SHOWA KAGAKU KIKAI CO., LTD.) using a 1.5 mmϕ punching screen to give a sieved powder.
(2) Crospovidone (Kollidon CL-F, BASF) (90 g) and sodium stearyl fumarate (18 g) were added to the obtained sieved powder (1692 g), and the mixture was mixed in a tumbler mixer (TM-15S, SHOWA KAGAKU KIKAI CO., LTD.) to give a mixed powder.
(3) The mixed powder was tableted by a rotary tableting machine (AQUARIUS 2L, Kikusui Seisakusho Ltd.) by using a 4 mmϕ punch (tableting pressure: 4 kN, weight per tablet: 30 mg) to give a core tablet with the following composition.
Composition of Preparation (30 mg)

| | |
|---|---|
| compound A | 1.0 mg |
| D-mannitol (in granules) | 20.45 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Comparative Example 5

(1) Hydroxypropylcellulose (HPC-L, NIPPON SODA CO., LTD.) (660 g) was dissolved in purified water (10230 g) to give a binding solution. Compound A (1320 g), lactose (DMV INTERNATIONAL) (16104 g), and corn starch (Japan Corn Starch Co., Ltd.) (2640 g) were uniformly mixed in a fluid bed dryer granulator (FD-S2, POWREX CORPORATION), granulated while spraying the binding solution (10890 g), and dried to give a granulated powder. This granulation step was performed twice. A part of the obtained granulated powder was ground by a power mill grinding machine (P-3, SHOWA KAGAKU KIKAI CO., LTD.) using a 1.5 mmφ punching screen to give a sieved powder.

(2) Corn starch (1013 g) and magnesium stearate (298 g) were added to the obtained sieved powder (37430 g), and the mixture was mixed in a tumbler mixer (TM20-0-0, Suchiro Kakoki Co., Ltd.) to give a mixed powder.

(3) The mixed powder was tableted by a rotary tableting machine (AQUARIUS 36K, Kikusui Seisakusho Ltd.) by using a 7 mmφ punch (tableting pressure: 7 kN, weight per tablet: 130 mg) to give a tablet (core tablet).

(4) Hydroxypropylmethylcellulose (TC-5R, Shin-Etsu Chemical Co., Ltd.) (1548 g) and Copovidone (310.5 g) were dissolved and dispersed in purified water (16150 g) to give dispersion I. Titanium oxide (207 g) and yellow ferric oxide (4.14 g) were dispersed in purified water (1822 g) to give dispersion II. Dispersion II was added to dispersion I, and the mixture was stirred to give a coating solution. Using a coater (High Coater HCF-100N, Freund Corporation), the coating solution was sprayed on the core tablet obtained in (3) until the weight of the core tablet increased by 5 mg per tablet to give a film-coated tablet having the following composition.

Composition of Preparation (135 mg)

| | |
|---|---|
| compound A | 8.0 mg |
| lactose | 97.6 mg |
| corn starch | 19.4 mg |
| hydroxypropylcellulose | 4.0 mg |
| magnesium stearate | 1.0 mg |
| hydroxypropylmethylcellulose | 3.74 mg |
| Copovidone | 0.75 mg |
| titanium oxide | 0.5 mg |
| yellow ferric oxide | 0.01 mg |
| total | 135 mg |

Example 8

(1) D-Mannitol (PEARLITOL 50C, Roquette) (510 g) was dissolved in purified water (2890 g) to give a coating solution. Compound A (17.05 g), D-mannitol (3114 g), microcrystalline cellulose (CEOLUS PH-101, Asahi Kasei Corporation) (127.5 g), and partly pregelatinized starch (PCS, Asahi Kasei Corporation) (510 g) were uniformly mixed in a fluid bed dryer granulator (FD-5S, POWREX CORPORATION), granulated while spraying the coating solution (3400 g), and dried to give a granulated powder. A part of the obtained granulated powder was sieved using a round sieve (mesh size 1.0 mmφ) to give sieved powder A.

(2) The same step as (1) was performed to give sieved powder B.

(3) To the obtained sieved powder A (3146.5 g) and sieved powder B (3146.5 g) were added crospovidone (Kollidon CL-F, BASF) (375.0 g), aspartame (750 g), vanillin (7.5 g) and sodium stearyl fumarate (75 g), and the mixture was mixed in a tumbler mixer (TM-60S, SHOWA KAGAKU KIKAI CO., LTD.) to give a mixed powder.

(4) The mixed powder was tableted by a rotary tableting machine (AQUARIUS 2L, Kikusui Seisakusho Ltd.) using a 4 mmφ punch (tableting pressure: 4 kN, weight per tablet: 30 mg) to give a core tablet with the following composition.

Composition of Preparation (30 mg)

| | |
|---|---|
| compound A | 0.1 mg |
| D-mannitol (in granules) | 18.32 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| aspartame | 3.0 mg |
| vanillin | 0.03 mg |
| total | 30 mg |

Example 9

(1) D-Mannitol (PEARLITOL 50C, Roquette) (510 g) was dissolved in purified water (2890 g) to give a coating solution. Compound A (68.20 g), D-mannitol (3063 g), microcrystalline cellulose (CEOLUS PH-101, Asahi Kasei Corporation) (127.5 g), and partly pregelatinized starch (PCS, Asahi Kasei Corporation) (510 g) were uniformly mixed in a fluid bed dryer granulator (FD-5S, POWREX CORPORATION), granulated while spraying the coating solution (3400 g), and dried to give a granulated powder. A part of the obtained granulated powder was sieved by using a round sieve (mesh size 1.0 mmφ) to give sieved powder A.

(2) The same step as (1) was performed to give sieved powder B.

(3) To the obtained sieved powder A (3146.5 g) and sieved powder B (3146.5 g) were added crospovidone (Kollidon CL-F, BASF) (375.0 g), aspartame (750 g), vanillin (7.5 g) and sodium stearyl fumarate (75 g), and the mixture was mixed in a tumbler mixer (TM-60S, SHOWA KAGAKU KIKAI CO., LTD.) to give a mixed powder.

(4) The mixed powder was tableted by a rotary tableting machine (AQUARIUS 2L, Kikusui Seisakusho Ltd.) using a 4 mmφ punch (tableting pressure: 4 kN, weight per tablet: 30 mg) to give a core tablet with the following composition.

Composition of Preparation (30 mg)

| | |
|---|---|
| compound A | 0.4 mg |
| D-mannitol (in granules) | 18.02 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| aspartame | 3.0 mg |
| vanillin | 0.03 mg |
| total | 30 mg |

Example 10

(1) D-Mannitol (PEARLITOL 50C, Roquette) (510 g) was dissolved in purified water (2890 g) to give a coating solution. Compound A (136.4 g), D-mannitol (2995 g), microcrystalline cellulose (CEOLUS PH-101, Asahi Kasei Corporation)

(127.5 g), and partly pregelatinized starch (PCS, Asahi Kasei Corporation) (510 g) were uniformly mixed in a fluid bed dryer granulator (FD-5S, POWREX CORPORATION), granulated while spraying the coating solution (3400 g), and dried to give a granulated powder. A part of the obtained granulated powder was sieved by using a round sieve (mesh size 1.0 mmϕ) to give sieved powder A.

(2) The same step as (1) was performed to give sieved powder B.

(3) To the obtained sieved powder A (3146.5 g) and sieved powder B (3146.5 g) were added crospovidone (Kollidon CL-F, BASF) (375.0 g), aspartame (750 g), vanillin (7.5 g) and sodium stearyl fumarate (75 g), and the mixture was mixed in a tumbler mixer (TM-60S, SHOWA KAGAKU KIKAI CO., LTD.) to give a mixed powder.

(4) The mixed powder was tableted by a rotary tableting machine (AQUARIUS 2L, Kikusui Seisakusho Ltd.) using a 4 mmϕ punch (tableting pressure: 4 kN, weight per tablet: 30 mg) to give a core tablet with the following composition.

Composition of Preparation (30 mg)

| | |
|---|---|
| compound A | 0.8 mg |
| D-mannitol (in granules) | 17.62 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| aspartame | 3.0 mg |
| vanillin | 0.03 mg |
| total | 30 mg |

Experimental Example 1

The tablet obtained in Example 1 was measured for the tablet hardness and disintegration time. The tablet hardness was measured by a tablet hardness tester (TH-303 MP, Toyama Sangyo CO., LTD.) (n=10). The disintegration time was measured by a disintegration tester (ODT-101, Toyama Sangyo CO., LTD.) (n=6). The results are shown in Table 1.

disintegration tester conditions
rotation number: 50 rpm
plummet: mmϕ, (10 g)

TABLE 1

| | |
|---|---|
| hardness | 21N |
| absolute hardness | 2.73 N/mm$^2$ |
| disintegration | 5.24 sec |

Experimental Example 2

The mixed powder obtained in Example 1 was measured for the dissolution property. The mixed powder (15 g) (corresponding to 500 mg of compound A) was placed in the Japanese Pharmacopoeia 2nd fluid (500 ml), and the dissolution property was evaluated by the Paddle Method, rotation number 25 rpm, 37° C. After adding the sample, the eluate was sampled with time (0.25 min, 0.5 min, 0.75 min, 1 min, 5 min, 15 min, 30 min), filtered by using a hydrophilic filter (0.45 μm), dissolved by 10-fold diluting with the extract (water/acetonitrile mixed solution (1:1)), and quantified by high performance liquid column chromatography (HPLC) under the following conditions to calculate the solubility. The results are shown in Table 2.

HPLC Conditions
detector: ultraviolet ray absorption spectrophotometer measurement wavelength: 240 nm
column: YMC-Pack ODS-AM AM-307, 5 μm, inner diameter: 4.6 mm
length: 75 mm
column temperature: 25° C.
mobile phase: 0.01 mol/L phosphate buffer/acetonitrile mixed solution (5:3)
flow: 1.2 ml/min

TABLE 2

| time (min) | compound A concentration (mg/ml) |
|---|---|
| 0 | 0 |
| 0.25 | 0.103 |
| 0.5 | 0.218 |
| 0.75 | 0.225 |
| 1 | 0.237 |
| 5 | 0.273 |
| 15 | 0.279 |
| 30 | 0.280 |

Experimental Example 3

The injections obtained in Comparative Examples 1, 3, oral tablets obtained in Comparative Examples 2, 4 and preparations for oral-mucosal absorption obtained in Examples 2-5 were measured for blood kinetics after intravenous injection, oral, sublingual and buccal administrations in *Macaca fascicularis* under fasting conditions. The plasma concentration before administration, and 5 min, 10 min, 15 min, 30 min, 60 min, 120 min, 240 min and 360 min after administration was measured, and the area under the plasma concentration time curve (AUC) was calculated according to the trapezoidal rule. In addition, bioavailability (BA) was determined by calculating the ratio of AUC by oral, sublingual or buccal administration to AUC by intravenous injection. The results are shown in Table 3.

TABLE 3

| dose (mg) | administration route | preparation | $T_{max}$ (min) | $C_{max}$ (ng/ml) | AUC (ng · min/ml) | BA (%) |
|---|---|---|---|---|---|---|
| 0.25 | intravenous injection | Comparative Example 1 | 9.0 ± 6.5 | 63.4 ± 14.1 | 2933.8 ± 578.5 | — |
| | oral | Comparative Example 2 | 132.0 ± 130.1 | 0.4 ± 0.1 | 54.4 ± 22.6 | 1.9 |
| | sublingual | Example 2 | 34.0 ± 15.2 | 12.5 ± 5.9 | 1218.0 ± 655.8 | 41.5 |
| | buccal | Example 6 | 36.0 ± 18.0 | 22.7 ± 12.3 | 1656.0 ± 726.0 | 56.4 |
| 1 | intravenous injection | Comparative Example 3 | 3.2 ± 1.6 | 509.7 ± 248.9 | 16889.5 ± 2057.2 | — |
| | oral | Comparative Example 4 | 8.0 ± 13.0 | 0.8 ± 1.2 | 21.3 ± 35.8 | 0.1 |

TABLE 3-continued

| dose (mg) | administration route | preparation | $T_{max}$ (min) | $C_{max}$ (ng/ml) | AUC (ng · min/ml) | BA (%) |
|---|---|---|---|---|---|---|
| | sublingual | Example 3 | 28.0 ± 4.5 | 38.5 ± 12.8 | 3062.4 ± 1129.9 | 18.1 |
| | | Example 4 | 42.0 ± 16.0 | 31.4 ± 8.6 | 3206.9 ± 809.9 | 19.0 |
| | | Example 5 | 48.0 ± 16.0 | 46.6 ± 13.8 | 4568.4 ± 1286.3 | 27.0 |
| | buccal | Example 7 | 36.0 ± 12.0 | 87.1 ± 21.2 | 5862.0 ± 1038.0 | 34.7 |

Experimental Example 4

Oral preparation and preparation for oral-mucosal absorption were measured for blood kinetics of unchanged form and active metabolite M-II after oral or sublingual administration to human. The plasma concentration before administration, and 5 min, 10 min, 15 min, 20 min, 30 min, 45 min, 60 min, 90 min, 120 min, 180 min, 240 min, 360 min, 480 min, 600 min, 720 min and 1440 min after administration was measured.

The results are shown in Table 4. To be specific, symbol/term and definition thereof in this table are explained in the following. The study was conducted by cross-over method under open-label condition.

AUC(0-tlqc): Area under the serum concentration-time curve from time 0 to time of the last quantifiable concentration (tlqc), calculated using the linear trapezoidal rule.

AUC(0-inf): Area under the serum concentration-time curve from time 0 to infinity, calculated as AUC(0-inf)=AUC(0-tlqc)+lqc/λz, where tlqc is the time of last quantifiable concentration and lqc is the last quantifiable concentration. λz: Terminal elimination rate constant, calculated as the negative of the slope of the log-linear regression of the natural logarithm concentration-time curve during the terminal phase.

Cmax: Maximum observed serum concentration.

Tmax: Time to reach Cmax.

Active metaboline M-II: (2S)-2-Hydroxy-N-{2-[(8S)-1,6,7,8-tetrahydro-2H-indeno[5,4-b]furan-8-yl]ethyl}propanamide

TABLE 4

| measurement substance | dose (mg) | administration route | preparation | Tmax(a) (hr) |
|---|---|---|---|---|
| unchanged form | 8 | Oral (n = 23) | Comparative Example 8 | 0.75 (0.33, 2.00) |
| | 0.5 | Sublingual (n = 24) | Example 6 (two tablets) | 0.25 (0.15, 0.50) |
| active metabolite M-II | 8 | Oral (n = 23) | Comparative Example 8 | 1.00 (0.50, 3.00) |
| | 0.5 | Sublingual (n = 24) | Example 6 (two tablets) | 0.75 (0.25, 1.00) |

| measurement substance | dose (mg) | Cmax (ng/ml) | AUC(0-tlqc) (ng · hr/ml) | AUC(0-inf) (ng · hr/ml) |
|---|---|---|---|---|
| unchanged form | 8 | 4.76 ± 5.208(b) (c)109 | 6.08 ± 6.374(b) (c)105 | 5.57 ± 5.765(b)(d) (c)104 |
| | 0.5 | 4.74 ± 1.508(b) (c)32 | 3.59 ± 1.077(b) (c)30 | 3.73 ± 1.124(b)(e) (c)30 |
| active metabolite | 8 | 68.10 ± 23.315(b) | 208.25 ± 83.426(b) | 212.45 ± 84.314(b) |
| M-II | 0.5 | 4.18 ± 1.247(b) (c)30 | 9.94 ± 4.677(b) (c)47 | 12.18 ± 4.790(b) (c)39 |

(a)Median (min, max) is presented.
(b)Mean ± SD is presented.
(c)Arithmetic Mean (% CV) is presented.
(d)n = 22
(e)n = 23

Example 11

A methylcellulose powder (0.5 g) was dissolved in water (99.5 g) under ice-cooling, and compound A (100 mg) was added to the obtained solution (10 ml), stirred and uniformly dispersed therein. The obtained suspension was filled in a spray device (spray amount: 100 μL/time) to give an oral spray preparation.

Example 12

Hydroxypropyl-β-cyclodextrin (HP-β-CyD) (40 g) was dissolved in water (60 g), and compound A (100 mg) was added to the obtained solution (10 ml), stirred and dissolved therein. The obtained solution was filled in a spray device (spray amount: 100 μL/time) to give an oral spray preparation.

Example 13

Compound A (100 mg), polyvinylpyrrolidone (1 g) and hydroxypropylcellulose (18 g) were added to ethanol (100 ml) and dissolved by stirring. The obtained solution (1 ml) was spread flat on a plastic sheet and dried to give an orally rapidly dissolving film preparation.

Example 14

Compound A (100 mg), D-mannitol (5 g) and hydroxypropylcellulose (100 mg) were added to a mixed solution (100 ml) of water and ethanol (4:1) and dissolved by stirring. The obtained solution (1 ml) was dispensed to a pocket of a blister pack with vinyl chloride resin as an inner film, frozen at −30° C., and dried by a vacuum dryer to give an orally rapidly dissolving freeze-dried preparation.

Experimental Example 5

Therapeutic Effectiveness on Maintenance of Remission Phase in Patients with Bipolar Disorder 1. Test Tablet
Oral 8 mg formulation containing Compound A
2. Test Method
The test tablet was administered to a group of patients suffering from bipolar disorder and in the remission phase, once daily at bedtime for 6 months. A placebo was administered once daily at bedtime to a separate control group of patients in the remission phase of bipolar disorder for 6 months. This study was performed as a double-blind, randomized, placebo-controlled trial. The time from randomization to relapse over 6 months of treatment is determined by the Primary Investigator (PI) or defined by any of the following criteria: depression [Montgomery-Asberg Depression Rating Scale (MADRS) score ≥16]; mania/hypomania [Young Mania Rating Scale (YMRS) total score ≥14]; clinical global impressions bipolar version (CGI-BP); cumulative proportion of participants in each arm (placebo or Compound A) surviving without relapse [MADRS score ≥16 and YMRS total score ≥14], a medication initiation or change for manic/depressed/mixed symptoms, a hospitalization for manic/depressed/mixed symptoms and suicide risk or imminent risk of suicide.

3. Test Result

The test results are presented in Table 5:

TABLE 5

|  | Compound A (Ramelteon) | Placebo |
|---|---|---|
| Number of Participants Analyzed | 42 | 41 |
| Cumulative Proportion of Patients in each arm surviving without relapse |  |  |
| Baseline | 1.00 | 1.00 |
| Month 1 | 0.929 | 0.951 |
| Month 2 | 0.849 | 0.588 |
| Month 3 | 0.716 | 0.448 |
| Month 4 | 0.661 | 0.384 |
| Month 5 | 0.632 | 0.320 |
| Month 6 | 0.566 | 0.320 |

As Table 5 demonstrates, the group of bipolar patients in the remission phase receiving Compound A had a greater survival rate than patients receiving the placebo. This demonstrates that Compound A is effective in treating bipolar patients and keeping them in the remission phase.

Experimental Example 6

Therapeutic Effectiveness on acute Depression in Patients with Bipolar Disorder

1. Test Tablet

Oral 8 mg formulation containing Compound A

2. Test Method

The test tablet was administered once daily to a group of patients suffering from bipolar disorder and in the mania phase for up to 8 weeks. A placebo was administered to a separate control group of patients in the mania phase of bipolar disorder for up to 8 weeks. This study was performed as a double-blind, randomized, placebo-controlled trial. The time from randomization to relapse over 6 months of treatment is determined by the Primary Investigator (PI) or defined by any of the following criteria: clinical global impressions scale for bipolar disorder (CGI-BP).

3. Test Result

Longitudinal analysis of change in outcome revealed a CGI-BP severity for depression of −0.1 (−0.16 to −0.05), wherein a value below 0 favors Compound A (95% CI; N=9; P value=0.001). This result indicates that Compound A might have decreased depressive symptoms.

Experimental Example 7

Pharmacokinetic Parameters

1. Test Protocol

A randomized, open-label study to assess the pharmacokinetic parameters of an oral-mucosal tablet containing Compound A and its bioavailability relative to an oral 8 mg tablet containing Compound A was performed.

The test was conducted in two parts: (1) a parallel-group design to evaluate the pharmacokinetic parameters of 3 doses of Compound A (0.25, 0.5 and 1 mg) in oral-mucosal tablets and (2) an open-label, randomized 2-period crossover design to assess the relative bioavailability (pharmacokinetic profile) of the oral-mucosal 0.5 mg tablet compared with the bioavailability of the oral 8 mg tablet.

For part (1), a total of 18 subjects were randomly assigned to 1 of the 3 dosing regimens (i.e., 0.25, 0.5 and 1 mg; 6 subjects per dose) and each subject received a single dose of Compound A at the assigned dose.

For part (2), a total of 24 subjects were randomly assigned to take either the oral-mucosal 0.5 mg tablet or the oral 8 mg tablet at a single dose during each of the two periods.

To evaluate the studies, the pharmacokinetic parameters of Compound A and M-II were measured, including maximum observed serum concentration (Cmax) and area under the serum concentration-time curve from time 0 to the last quantifiable concentration (AUC(0-tlqc)).

2. Test Results

Figure 2:
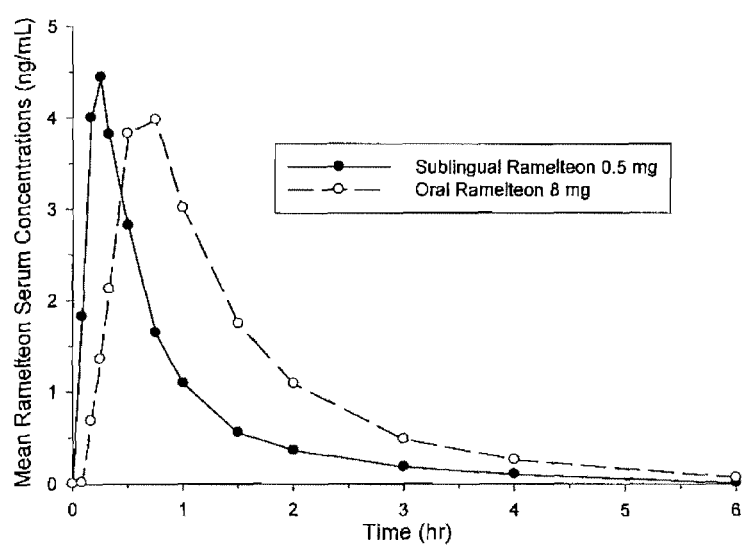
FIG. 2 demonstrates the mean serum concentration of compound A after oral-mucosal delivery compared to the concentration of compound A after oral delivery.
Figure 3:
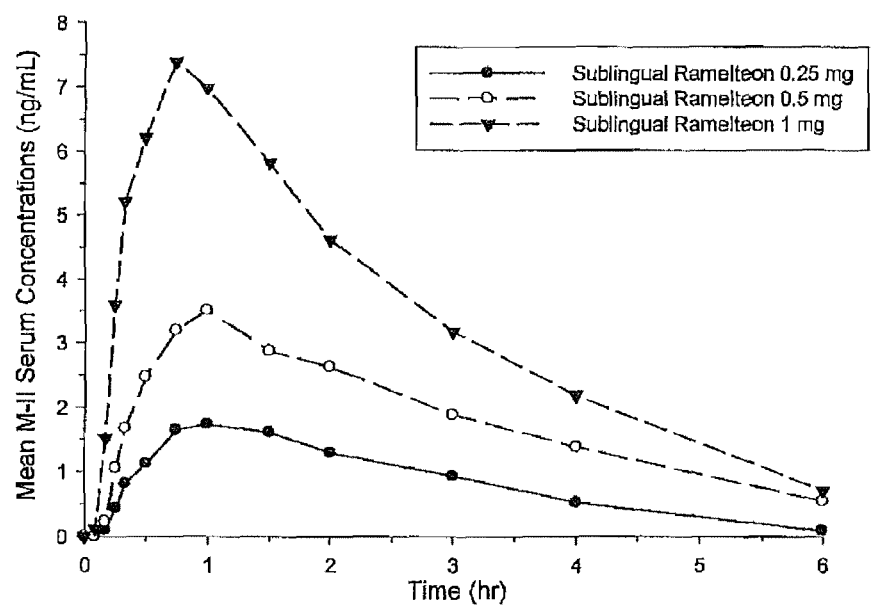
FIG. 3 demonstrates the mean serum concentration of metabolite M-II after oral-mucosal delivery at different concentrations.
Figure 4:
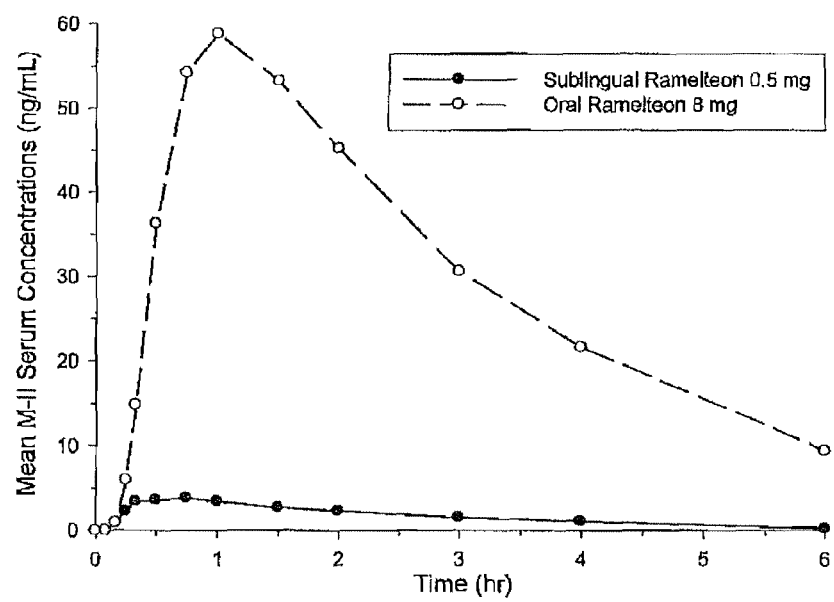
FIG. 4 demonstrates the mean serum concentration of metabolite M-II after oral-mucosal delivery compared to the concentration of M-II after oral delivery.

The results of the test are provided in the two tables below and in FIGS. 1 and 2.

For part (1), the mean Cmax and AUC(0-tlgc) values of Compound A increased with oral-mucosal dose in a dose proportional manner between 0.25 and 0.5 mg and in a less than dose proportional manner between 0.5 and 1.0 mg. M-II values increased with oral-mucosal dose in an apparent dose proportional manner between 0.25 and 1.0 mg. The intersubject variability for both Compound A and M-II ranged from 11% to 66%.

For part (2), regarding Cmax and AUC(0-tlqc), much larger inter-subject variability for the oral 8 mg table (% CV ranges from 104% to 109%) than for the oral-mucosal tables (% CV ranges from 30% to 32%) was observed. The geometric means for Cmax and AUC(0-tlqc) were considered more appropriate than arithmetic means for comparison purposes, revealing that the mean Cmax values of Compound A after oral-mucosal administration were greater compared to oral administration of the 8 mg tablet. The geometric mean of AUC(0-tlqc) for Compound A were similar between the oral-mucosal and oral administrations. Also, the geometric mean Cmax and AUC(0-tlqc) values of M-II were much lower after oral-mucosal administration when compared with M-II after administration of the oral tablet. The inter-subject variability values for M-II were similar between both the oral-mucosal and oral regimes, ranging from 18% to 47%.

Therefore, the 0.5 mg oral-mucosal dose provided an increase in maximum exposure (as measured by Cmax) and similar total exposure (as measured by AUC) to Compound A compared to the oral 8 mg tablet. Correspondingly, the oral-mucosal administration provided a small fraction of exposure (<7%) to M-II compared to the approved oral 8 mg tablet.

| measurement substance | Dose (mg) | Statistic | Cmax (ng/ml) | AUC(0-tlqc) (ng · hr/ml) |
|---|---|---|---|---|
| unchanged form of compound A | 0.25 | N | 6 | 6 |
| | | Mean | 3.14 | 2.60 |
| | | SD | 1.260 | 0.780 |
| | | % CV | 40 | 30 |
| | 0.5 | N | 6 | 6 |
| | | Mean | 5.85 | 6.23 |
| | | SD | 2.009 | 4.026 |
| | | % CV | 34 | 65 |
| | 1 | N | 6 | 6 |
| | | Mean | 9.57 | 7.87 |
| | | SD | 2.372 | 2.916 |
| | | % CV | 25 | 37 |
| active metabolite M-II | 0.25 | N | 6 | 6 |
| | | Mean | 1.85 | 4.64 |
| | | SD | 0.717 | 2.887 |
| | | % CV | 39 | 62 |
| | 0.5 | N | 6 | 6 |
| | | Mean | 3.74 | 10.53 |
| | | SD | 1.093 | 4.059 |
| | | % CV | 29 | 39 |
| | 1 | N | 6 | 6 |
| | | Mean | 7.68 | 20.18 |
| | | SD | 2.821 | 5.538 |
| | | % CV | 37 | 27 |

Based on the data above as well as the data presented in Table 4, the predicted pharmacokinetic parameters for 0.1 mg, 0.4 mg and 0.8 mg sublingual tablets were calculated using the following method.

A 2 compartment model for the unchanged form of compound A and 1 compartment model for its metabolite M-II was used to fit PK profiles after the administration of 0.25 mg, 0.5 mg and 1 mg doses, respectively. The Bayesian parameter estimates were subsequently mapped such that individual parameter estimates for 0.25 mg, 0.5 mg, and 1 mg doses corresponded to the 0.1 mg, 0.4 mg, and 0.8 mg doses, respectively, during simulation. Descriptive statistics were calculated based on the individual simulated Cmax and AUC values including geometric mean and corresponding 95% and 80% lower and upper geometric mean confidence intervals (CI).

The predicted geometric mean values and the geometric mean confidence intervals thus obtained are shown in the following.

| Dose (mg) | Cmax (ng/mL) | AUC(0-tlqc) (ng · hr/mL) |
|---|---|---|
| Predicted Compound A Exposure | | |
| Geometric Mean (Lower-Upper Geometric 95% CI) | | |
| 0.1 | 1.17 (0.43-3.13) | 1.04 (0.48-2.26) |
| 0.4 | 3.75 (2.04-6.89) | 3.18 (1.52-6.68) |
| 0.8 | 7.15 (3.63-14.06) | 5.98 (2.48-14.43) |
| Predicted M-II Exposure | | |
| 0.1 | 0.69 (0.29-1.66) | 1.97 (0.56-6.97) |
| 0.4 | 3.02 (1.76-5.18) | 8.57 (3.80-19.29) |
| 0.8 | 5.65 (2.26-14.10) | 17.49 (10.42-29.36) |
| Predicted Compound A Exposure | | |
| Geometric Mean (Lower-Upper Geometric 80% CI) | | |
| 0.1 | 1.17 (0.66-2.05) | 1.04 (0.67-1.62) |
| 0.4 | 3.75 (2.54-5.54) | 3.18 (1.98-5.12) |
| 0.8 | 7.15 (4.85-10.54) | 5.98 (3.60-9.91) |
| Predicted M-II Exposure | | |
| 0.1 | 0.69 (0.42-1.14) | 1.97 (0.95-4.07) |
| 0.4 | 3.02 (2.13-4.27) | 8.57 (5.09-14.41) |
| 0.8 | 5.65 (3.34-9.55) | 17.49 (13.0-23.55) |

Experimental Example 8

Therapeutic Effectiveness on Maintenance (Maintenance of Remission Phase of Bipolar Disorder)

1. Test Tablet

The Sublingual Formulations of Example 8, Example 9 and Example 10

2. Test Method

The test tablet is administered sublingually to a patient at the remission phase of bipolar disorder once every night at bedtime for up to 9 months. Primary outcome can be measured according to the time from randomization to relapse events. The time from randomization to relapse over 9 months treatment period as determined by the Primary Investigator (PI) or defined by any of the following criteria: depression [Montgomery-Åsberg Depression Rating Scale (MADRS) score ≥16]; mania/hypomania [Young Mania Rating Scale (YMRS) total score ≥14]; mixed episode [MADRS score ≥16 and YMRS total score ≥14]; or, whether participant receives psychiatric hospitalization for bipolar disorder, electroconvulsive therapy or any psychotropic medication change prescribed for the treatment of depression, mania/hypomania or mixed episodes.

3. Test Result

Compound A is expected to be quite effective on maintenance therapy of bipolar disorder at all doses.

Experimental Example 9

Therapeutic Effectiveness on Acute Depression (a Depression Symptom Associated with the Bipolar Disorder)

1. Test Tablet

The sublingual formulations of Example 8, Example 9 and Example 10

2. Test Method

The test tablet is administered sublingually to a patient suffering from bipolar disorder once daily at night time for up to 8 weeks. Primary outcome can be measured according to change from baseline in the Montgomery-Åsberg Depression Rating Scale (MADRS) total score at week 8. MADRS is a 10-item clinician rated scale to measure overall severity of depressive symptoms (i.e., apparent sadness, reported sadness, inner tension, etc.) rated on a 7-point Likert scale from 0 (normal) to 6 (most abnormal) with a total score range from 0 to 60. Higher scores indicate greater severity of symptoms.

3. Test Result

Compound A is expected to be quite effective on acute depression at all doses.

INDUSTRIAL APPLICABILITY

The present invention can provide a novel preparation showing improved bioavailability of a medicament and a production method thereof and the like.

When compound A is administered nasally (through nasal mucosa) to a human subject, it is expected to be effective on prophylaxis and/or treatment of bipolar disease as administered oral-mucosally as disclosed above. Compound A can be administered, for example, in the form of the formulation as disclosed in WO 01/15735.

When compound A is administered to a human subject, it can be also administered in the dosage forms suitable for inhalation (e.g. nebulizer, etc) in order to prevent and/or treat bipolar disease. The dosage forms can be produced according to a general production method in this art. The dose of compound A can be decided referring to, for example, the preparations (A) to (D) in the present application.

This application is based on patent application Nos. 2011-007371 and 2011-227333 filed in Japan, international application No. PCT/JP2012/051279, and U.S. application Ser. Nos. 13/261,266 and 13/491,887, the contents of which are incorporated in full herein.

The invention claimed is:

1. A method for the treatment of a bipolar disorder comprising administering daily 0.1 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 0.43 to about 3.13 ng/ml and AUC (0-tlqc) for compound A falls within the range of about 0.48 to about 2.26 ng·hr/ml.

2. The method according to claim 1, wherein the oral-mucosal administration is sublingual administration or buccal administration.

3. The method according to claim 1, wherein the bipolar disorder is bipolar disorder I.

4. The method according to claim 1, wherein the treatment of a bipolar disorder is a treatment of a depression symptom associated with the bipolar disorder or maintenance of a remission phase of the bipolar disorder.

5. The method according to claim 1, wherein in the fasting state, Cmax for compound A falls within the range of about 0.66 to about 2.05 ng/ml and AUC (0-tlqc) for compound A falls within the range of about 0.67 to about 1.62 ng·hr/ml.

6. The method according to claim 5, wherein the oral-mucosal administration is sublingual administration or buccal administration.

7. The method according to claim 5, wherein the bipolar disorder is bipolar disorder I.

8. The method according to claim 5, wherein the treatment of a bipolar disorder is a treatment of a depression symptom associated with the bipolar disorder or maintenance of a remission phase of the bipolar disorder.

9. A method for the treatment of a bipolar disorder comprising administering daily 0.4 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 2.04 to about 6.89 ng/ml and AUC (0-tlqc) for compound A falls within the range of about 1.52 to about 6.68 ng·hr/ml.

10. The method according to claim 9, wherein the oral-mucosal administration is sublingual administration or buccal administration.

11. The method according to claim 9, wherein the bipolar disorder is bipolar disorder I.

12. The method according to claim 9, wherein the treatment of a bipolar disorder is a treatment of a depression symptom associated with the bipolar disorder or maintenance of a remission phase of the bipolar disorder.

13. The method according to claim 9, wherein in the fasting state, Cmax for compound A falls within the range of about 2.54 to about 5.54 ng/ml and AUC (0-tlqc) for compound A falls within the range of about 1.98 to about 5.12 ng·hr/ml.

14. The method according to claim 13, wherein the oral-mucosal administration is sublingual administration or buccal administration.

15. The method according to claim 13, wherein the bipolar disorder is bipolar disorder I.

16. The method according to claim 13, wherein the treatment of a bipolar disorder is a treatment of a depression symptom associated with the bipolar disorder or maintenance of a remission phase of the bipolar disorder.

17. A method for the treatment of a bipolar disorder comprising administering daily 0.8 mg of (S)—N-[2-(1,6,7,8-tetrahydro-2H-indeno[5,4-b]furan-8-yl)ethyl]propionamide (compound A) to the oral mucosa of a human in need thereof, wherein in the fasting state, Cmax for compound A falls within the range of about 3.63 to about 14.06 ng/ml and AUC (0-tlqc) for compound A falls within the range of about 2.48 to about 14.43 ng·hr/ml.

18. The method according to claim 17, wherein the oral-mucosal administration is sublingual administration or buccal administration.

19. The method according to claim 17, wherein the bipolar disorder is bipolar disorder I.

20. The method according to claim 17, wherein the treatment of a bipolar disorder is a treatment of a depression symptom associated with the bipolar disorder or maintenance of a remission phase of the bipolar disorder.

21. The method according to claim 17, wherein in the fasting state, Cmax for compound A falls within the range of about 4.85 to about 10.54 ng/ml and AUC (0-tlqc) for compound A falls within the range of 3.60 to about 9.91 ng·hr/ml.

22. The method according to claim 21, wherein the oral-mucosal administration is sublingual administration or buccal administration.

23. The method according to claim 21, wherein the bipolar disorder is bipolar disorder I.

24. The method according to claim 21, wherein the treatment of a bipolar disorder is a treatment of a depression symptom associated with the bipolar disorder or maintenance of a remission phase of the bipolar disorder.

* * * * *